(12) United States Patent
Okuda

(10) Patent No.: US 12,303,298 B2
(45) Date of Patent: May 20, 2025

(54) METHODS AND SYSTEMS FOR ANALYZING A CENTRAL NERVOUS SYSTEM BASED ON BRAINSTEM STRUCTURAL CHARACTERISTICS

(71) Applicant: THE BOARD OF REGENTS OF THE UNIVERSITY OF TEXAS SYSTEM, Austin, TX (US)

(72) Inventor: Darin T. Okuda, Coppell, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 17/996,480

(22) PCT Filed: Apr. 23, 2021

(86) PCT No.: PCT/US2021/028898
§ 371 (c)(1),
(2) Date: Oct. 18, 2022

(87) PCT Pub. No.: WO2021/222029
PCT Pub. Date: Nov. 4, 2021

(65) Prior Publication Data
US 2023/0165467 A1    Jun. 1, 2023

Related U.S. Application Data

(60) Provisional application No. 63/018,103, filed on Apr. 30, 2020.

(51) Int. Cl.
*A61B 5/00* (2006.01)
*A61B 5/055* (2006.01)
(Continued)

(52) U.S. Cl.
CPC .......... *A61B 5/7275* (2013.01); *A61B 5/0042* (2013.01); *A61B 5/055* (2013.01);
(Continued)

(58) Field of Classification Search
CPC ..... A61B 5/7275; A61B 5/0042; A61B 5/055; A61B 5/4064; A61B 5/407; A61B 5/4076;
(Continued)

(56) References Cited

U.S. PATENT DOCUMENTS

2005/0233328 A1   10/2005   Berghs et al.
2011/0218253 A1   9/2011    Lange et al.
(Continued)

FOREIGN PATENT DOCUMENTS

WO    WO 2020/069509    4/2020
WO    WO 2021/222529    4/2021

OTHER PUBLICATIONS

U.S. Appl. No. 17/905,069, filed Aug. 26, 2022, Okuda.
(Continued)

*Primary Examiner* — Baisakhi Roy
*Assistant Examiner* — Kaitlyn E Sebastian
(74) *Attorney, Agent, or Firm* — Norton Rose Fulbright US LLP

(57) ABSTRACT

Some methods of analyzing one or more sections of a central nervous system of a patient comprise, for each of the section(s), from data the includes one or more 3D representations of the section, segmenting each of the 3D representation(s) into ventral and dorsal portions and, for at least one of the 3D representation(s), determining a mean curvature of at least a region of a surface of the dorsal portion and/or a mean curvature of at least a region of a surface of the ventral portion. Each of the section(s) can include at least a portion of a brainstem of the patient.

32 Claims, 13 Drawing Sheets

(51) Int. Cl.
  *G06T 7/00* (2017.01)
  *G06T 7/11* (2017.01)
  *G06T 7/38* (2017.01)
  *G06T 7/62* (2017.01)
  *G06T 7/64* (2017.01)
  *G06V 10/25* (2022.01)

(52) U.S. Cl.
  CPC ............ *A61B 5/4064* (2013.01); *A61B 5/407* (2013.01); *A61B 5/4076* (2013.01); *A61B 5/4842* (2013.01); *G06T 7/0012* (2013.01); *G06T 7/11* (2017.01); *G06T 7/38* (2017.01); *G06T 7/62* (2017.01); *G06T 7/64* (2017.01); *G06V 10/25* (2022.01); *G06T 2207/10088* (2013.01); *G06T 2207/30016* (2013.01); *G06T 2207/30096* (2013.01)

(58) Field of Classification Search
  CPC ....... A61B 5/4842; G06T 7/0012; G06T 7/11; G06T 7/38; G06T 7/62; G06T 7/64; G06T 2207/10088; G06T 2207/30016; G06T 2207/30096; G06V 10/25
  See application file for complete search history.

(56) References Cited

U.S. PATENT DOCUMENTS

| | | | |
|---|---|---|---|
| 2011/0313323 A1 | 12/2011 | Henderson et al. | |
| 2012/0277572 A1* | 11/2012 | Hubbard | A61B 5/055 600/419 |
| 2013/0150922 A1* | 6/2013 | Butson | G16H 20/40 607/46 |
| 2020/0100732 A1 | 4/2020 | Zizi et al. | |

OTHER PUBLICATIONS

International Search Report and Written Opinion in corresponding PCT Application No. PCT/US2021/028898, mailed Aug. 23, 2021.
International Search Report issued in PCT Application No. PCT/US2021/029835, mailed Sep. 8, 2021.
International Preliminary Report on Patentability issued in Corresponding PCT Application No. PCT/US2021/028898, mailed Aug. 23, 2021.
International Preliminary Report on Patentability issued in Corresponding PCT Application No. PCT/US2021/029835, mailed Sep. 8, 2021.
Moog, TM, et al., "African Americans experience disproportionate neurodegenerative changes in the medulla and upper cervical spinal cord in early multiple sclerosis", *Multiple Sclerosis and Related Disorders*, 45, 102429, 2020.
Sivakolundu et al., "BOLD signal within and around white matter lesions distinguishes multiple sclerosis and non-specific white matter disease: a three dimensional approach", *J. Neurol.*, 267(10), 2888-2896, 2020.
Calloni et al., "Multiparametric MR imaging of Parkinsonisms at 3 tesla: Its role in the differentiation of idiopathic Parkinson's disease versus atypical Parkinsonian disorders" *European Journal of Radiology* 2018, 109, pp. 95-100.
Extended European Search Report issued in Corresponding European Application No. 21797087.0, dated Apr. 18, 2024.
Reich et al., "Multiparametric magnetic resonance imaging analysis of the corticospinal tract in multiple sclerosis" *NeuroImage* 2007, 38, pp. 271-279.

* cited by examiner

METHODS AND SYSTEMS FOR ANALYZING A CENTRAL NERVOUS SYSTEM BASED ON BRAINSTEM STRUCTURAL CHARACTERISTICS

CROSS-REFERENCE TO RELATED APPLICATIONS

This application is a national phase application under 35 U.S.C § 371 of International Application No. PCT/US2021/028898, filed 23 Apr. 2021, which claims the benefit of priority of U.S. Provisional Patent Application No. 63/018,103, filed 30 Apr. 2020, the entire contents of each of which are hereby incorporated by reference in their entireties.

FIELD OF INVENTION

The present invention relates generally to analyzing the central nervous system of patients, including diagnosing and assessing the progression of multiple sclerosis.

BACKGROUND

Diseases such as multiple sclerosis (MS), Alzheimer's disease, neuromyelitis optica spectrum disorder (NMOSD), cerebrovascular accidents, non-specific white matter disease (NSWM), anti-myelin oligodendrocyte glycoprotein (MOG) syndrome, metachromatic leukodystrophy, mitochondrial disorders, and paraneoplastic antibody syndrome can affect the structures of the central nervous system. MS, for example, is a chronic autoimmune disorder of the central nervous system that results in myelin and axonal injury and subsequent neurodegeneration.

The diagnosis and assessment of such diseases are based on both clinical and radiological assessments of damage disseminated in both time and space. For example, studies have assessed the surface areas and volumes of portions of the central nervous system—such as portions of the spinal cord and brainstem—in subjects having neurological disorders such as MS in an attempt to develop criteria for disease diagnosis and the assessment of disease states. Another radiological assessment for MS includes determining whether a requisite number of lesions in the periventricular, juxtacortical, infratentorial, and spinal cord regions have a specific character (e.g., size, shape, and morphology) and spatial distribution patterns indicative of MS.

However, such assessments face challenges. For MS lesion analysis, effective application of the existing dissemination in space criteria may be hindered by the highly sensitive nature of magnetic resonance imaging (MRI) technology, the heterogeneity of lesions resulting from a variety of medical conditions, concomitant radiological features resulting from age-related changes and disease, and the lack of additional radiological characteristics beyond two-dimensional (2D) descriptions. Differences between subjects, such as race and ethnicity, may similarly detract from the reliability and uniform applicability of other criteria, as a diverse number of racial and ethnic groups have not been successfully incorporated into pivotal studies used for the generation of existing MS diagnostic criteria or in later-phase clinical trials. Accordingly, there is a need in the art for analytical techniques that can more reliably diagnose neurological diseases such as MS, permit distinctions between disease states, and facilitate personalized assessment and interventions.

SUMMARY

The present methods and systems address this need in the art through textural analysis of one or more sections of the central nervous system. The textural analysis can include, for each of the section(s), determining a mean curvature of at least a region of the surface of the section from data that includes one or more 3-dimensional (3D) representations thereof. Furthermore, each of the 3D representation(s) can be segmented into ventral and dorsal portions and the textural analysis can be performed for the surface of each of the portions. Such a textural analysis can yield information that facilitates diagnosis of neurological disorders and the assessment of the progression thereof for a wide range of patients, including those of different races and ethnicities.

Section(s) of the central nervous system that can be analyzed include those that comprise at least a portion of the brainstem, such as a first section that comprises the pons and/or a second section that comprises the medulla and the upper cervical spinal cord. To illustrate, for the diagnosis of MS, the mean curvature of a region of the pons's ventral portion can differ amongst healthy patients, patients having non-progressive MS, patients having progressive MS, and patients of different ethnicities, allowing for reliable diagnosis of MS even before clinical symptoms manifest. Rates of change in mean curvature can also vary between at least some of such groups. In the pons, progressive MS patients and non-progressive MS patients that are Black can exhibit greater mean curvature changes toward concavity than healthy and white non-progressive MS patients in the ventral portion thereof, whereas in the dorsal portion non-progressive white MS patients can have a baseline mean curvature similar to that of healthy patients but exhibit larger changes toward convexity than the other cohorts. In the dorsal portion of the medulla and upper cervical spinal cord, Black non-progressive MS patients can exhibit greater changes in mean curvature toward concavity than healthy and white non-progressive MS patients. Such information regarding changes in surface curvature, along with ethnicity information, can further facilitate the diagnosis of MS and the assessment of rates of neurodegeneration, including in clinical trials for determining the efficacy of a treatment.

The textural analysis can be supplemented with an assessment of the volume and/or surface area of the brainstem or portions thereof. While healthy and white non-progressive MS patients may exhibit steady or growing brainstem volumes and surface areas, Black non-progressive MS patients—like progressive MS patients—can have brainstem volumes and surface areas that decrease over time. Measurements of the change in brainstem volume and surface area, along with ethnicity information, can thus further facilitate the diagnosis and assessment of MS in a patient.

Some methods of analyzing one or more sections of a central nervous system comprise, for each of the section(s), from data that includes one or more 3-dimensional (3D) representations of the section, segmenting each of the 3D representation(s) into ventral and dorsal portions, and for at least one of the 3D representation(s), determining a mean curvature of at least a region of a surface of the dorsal portion and/or a mean curvature of at least a region of a surface of the ventral portion. Some systems for analyzing one or more sections of a central nervous system of a patient comprises one or more processors configured to, for each of the section(s), from data that includes one or more 3-dimensional (3D) representations of the section, segment each of the 3D representation(s) into ventral and dorsal portions, and for at least one of the 3D representation(s), determine a mean curvature of at least a region of a surface of the dorsal portion and/or a mean curvature of at least a region of a surface of the ventral portion. Each of the section(s), in some embodiments, includes at least a portion of a brainstem of the patient. A first one of the section(s), in some embodiments, includes a pons of the patient. A second one of the section(s), in some embodiments, includes a medulla and upper cervical spinal cord of the patient.

Some methods comprise characterizing and in some systems the processor(s) are configured to characterize whether the patient has multiple sclerosis and/or a type of multiple sclerosis in the patient based at least in part on the mean curvature of the region of the surface of the dorsal portion of the first section and/or the mean curvature of the region of the surface of the ventral portion of the first section. In embodiments, the characterization is based at least in part on an ethnicity of the patient. In some systems, the processor(s) are configured to determine that the patient has progressive multiple sclerosis when the mean curvature of the region of the surface of the dorsal portion of the first section is greater than or equal to −1.0 millimeters (mm) and/or the mean curvature of the region of the surface of the ventral portion of the first section is less than or equal to −2.0 mm. In some methods, the characterizing comprises determining that the patient has progressive multiple sclerosis and, for the first section, the mean curvature of the region of the surface of the dorsal portion greater than or equal to −1.0 millimeters (mm) and/or the mean curvature of the region of the surface of the ventral portion is less than or equal to −2.0 mm. In some methods, the characterizing comprises determining that the patient has relapsing-remitting multiple sclerosis, for the first section, the mean curvature of the region of the surface of the dorsal portion is less than −1.0 millimeters (mm), and the patient is white.

Some methods comprising characterizing and in some systems the processor(s) are configured to characterize whether the patient has multiple sclerosis and/or a type of multiple sclerosis in the patient based at least in part on the mean curvature of the surface of the dorsal portion of the second section. In some embodiments, the characterizing comprises determining that the patient has multiple sclerosis, for the second section the mean curvature of the region of the surface of the dorsal portion is greater than or equal to 1.0 millimeter (mm), and the patient is Black.

In some embodiments, for each of the section(s), the one or more 3D representations include a 3D representation of the section at a first time and a 3D representation of the section at a second time that is after the first time. Some methods comprise determining and in some systems the processor(s) are configured to determine a rate of change, from the first time to the second time, in the mean curvature of the region of the surface of the dorsal portion of the first section; and/or a rate of change, from the first time to the second time, in the mean curvature of the region of the surface of the ventral portion of the first section. Some of such methods comprise characterizing and in some of such systems the processor(s) are configured to characterize whether the patient has multiple sclerosis and/or the type of multiple sclerosis in the patient based at least in part on the rate of change in the mean curvature of the region of the surface of the dorsal portion of the first section and/or the rate of change in the mean curvature of the region of the surface of the ventral portion of the first section. Some methods comprise characterizing and in some embodiments the processor(s) are configured to characterize an efficacy of a treatment administered to the patient based at least in part on the rate of change in the mean curvature of the region of the surface of the dorsal portion of the first section and/or the rate of change in the mean curvature of the region of the surface of the ventral portion of the first section.

Some methods comprise determining and in some systems the processor(s) are configured to determine a rate of change, from the first time to the second time, in the mean curvature of the region of the surface of the dorsal portion of the second section. Some methods comprise characterizing and in some systems the processor(s) are configured to characterize whether the patient has multiple sclerosis and/or a type of multiple sclerosis in the patient based at least in part on the rate of change in the mean curvature of the region of the surface of the dorsal portion of the second section. In some of such embodiments, the characterizing comprises determining that the patient has non-progressive multiple sclerosis, the rate of change in the mean curvature of the region of the surface of the dorsal portion is less than or equal to −1.0 millimeter (mm) per year, and the patient is Black.

Some methods comprise comparing and in some systems the processor(s) are configured to compare, for the first section, for at least one of the rate of change in the mean curvature of the region of the surface of the dorsal portion and the rate of change in the mean curvature of the region of the surface of the ventral portion, comparing the rate of change to a baseline rate of change. Some methods comprise comparing and in some systems the processor(s) are configured to compare, for the second section, the rate of change in the mean curvature of the dorsal portion to a baseline rate of change.

Some methods comprise determining and in some systems the processor(s) are configured to determine, from the data, a rate of change, from a first time to a second time that is after the first time, in a volume of at least a portion of the brainstem of the patient and/or a rate of change, from the first time to the second time, in a surface area of at least a portion of the brainstem of the patient. In some of such embodiments, some methods comprise determining and in some systems the processor(s) are configured to determine that the patient has non-progressive multiple sclerosis, the patient is Black, and the rate of change in the volume is less than or equal to 0 cubic millimeters ($mm^3$) per year and/or the rate of change in the surface area is less than or equal to 0 square millimeters ($mm^2$) per year.

In some embodiments, for each of the section(s), the dorsal and ventral portions each have a volume that is between 40% and 60% of a volume of the section. In some embodiments, the data comprises one or more magnetic resonance imaging (MRI) images that comprise the 3D representation(s) of the section(s). In some embodiments, for each of the section(s), each of the 3D representation(s) of the section comprises a polyhedron having a plurality of polygonal faces. In some of such embodiments, for at least one of the dorsal and ventral portions of at least one of the 3D representation(s) of the section, determining the mean curvature of the region of the portion comprises calculating a curvature of each of the polygonal faces of the region of the portion of the 3D representation based at least in part on a curvature calculated at each of a plurality of vertices of the polygonal face, and averaging the maximum curvatures of the polygonal faces of the region of the portion of the 3D representation.

The terms "a" and "an" are defined as one or more unless this disclosure explicitly requires otherwise. The terms "substantially" and "about" each is defined as largely but not necessarily wholly what is specified—and includes what is specified; e.g., substantially or about 90 degrees includes 90 degrees and substantially or about parallel includes parallel—as understood by a person of ordinary skill in the art. In any disclosed embodiment, the terms "substantially" and "about" may each be substituted with "within [a percentage] of" what is specified, where the percentage includes 0.1, 1, 5, and 10 percent.

The terms "comprise" and any form thereof such as "comprises" and "comprising," "have" and any form thereof such as "has" and "having," and "include" and any form thereof such as "includes" and "including" are open-ended linking verbs. As a result, a system that "comprises," "has," or "includes" one or more elements possesses those one or more elements, but is not limited to possessing only those elements. Likewise, a method that "comprises," "has," or "includes" one or more steps possesses those one or more steps, but is not limited to possessing only those one or more steps.

Any embodiment of any of the systems and methods can consist of or consist essentially of—rather than comprise/include/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Further, a system or component thereof that is configured in a certain way is configured in at least that way, but it can also be configured in other ways than those specifically described.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIGS. 7B and 7C each include 3D representations of the brainstem at a first time (solid) and at a second time (mesh), respectively, superimposed on one another.

FIGS. 8B and 8C each include 3D representations of the brainstem at a first time (mesh) and at a second time (solid), respectively, superimposed on one another.

FIGS. 9B and 9C each include 3D representations of the brainstem at a first time (mesh) and at a second time (solid), respectively, superimposed on one another.

FIGS. 10B and 10C each include 3D representations of the brainstem at a first time (solid) and at a second time (mesh), respectively, superimposed on one another.

FIGS. 11B and 11C each include 3D representations of the brainstem at a first time (mesh) and at a second time (solid), respectively, superimposed on one another.

DETAILED DESCRIPTION

Figure 1:
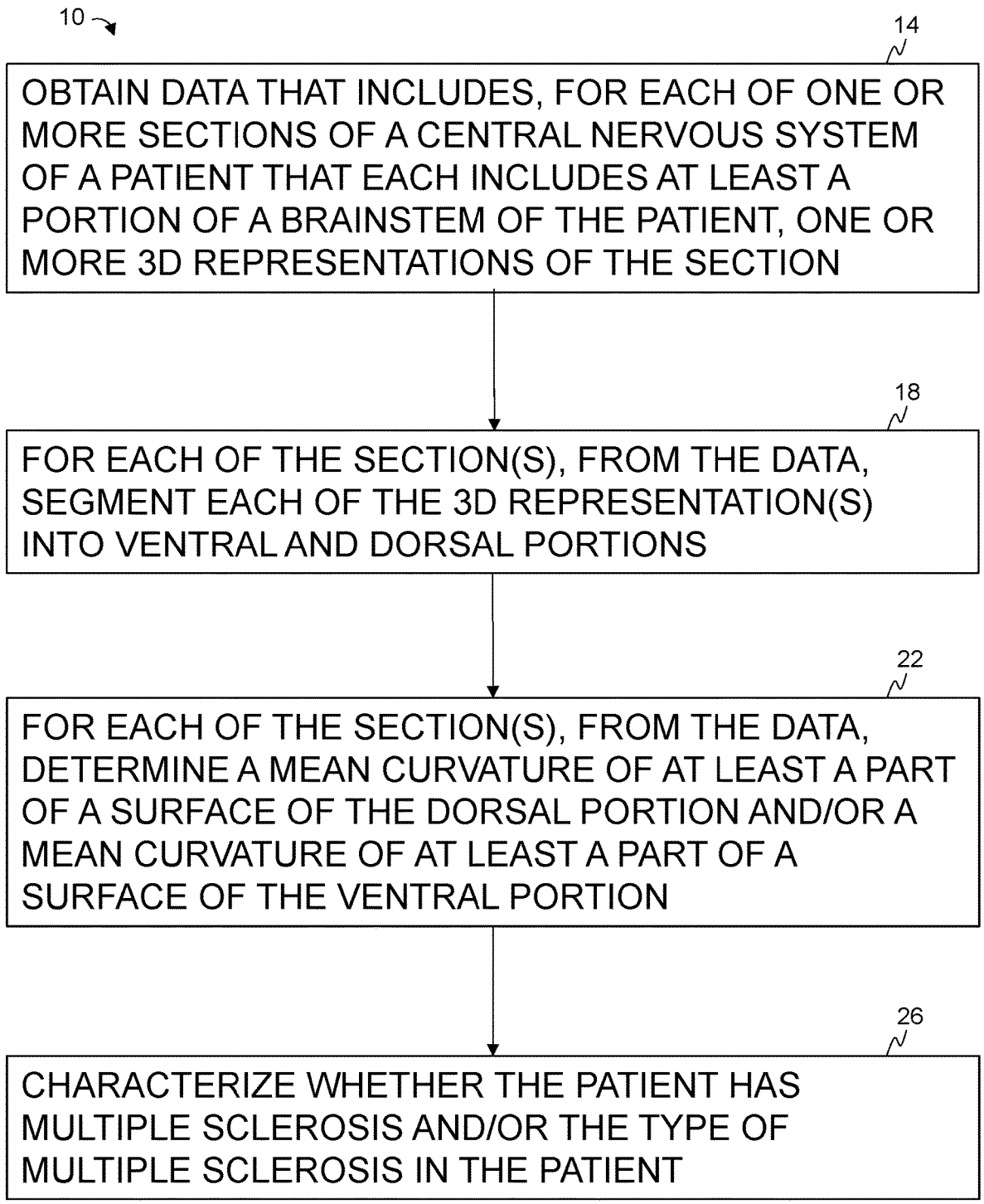
FIG. 1 illustrates some of the present methods of analyzing one or more sections of a central nervous system of a patient using data that includes one or more 3D representations thereof.
Figure 2:
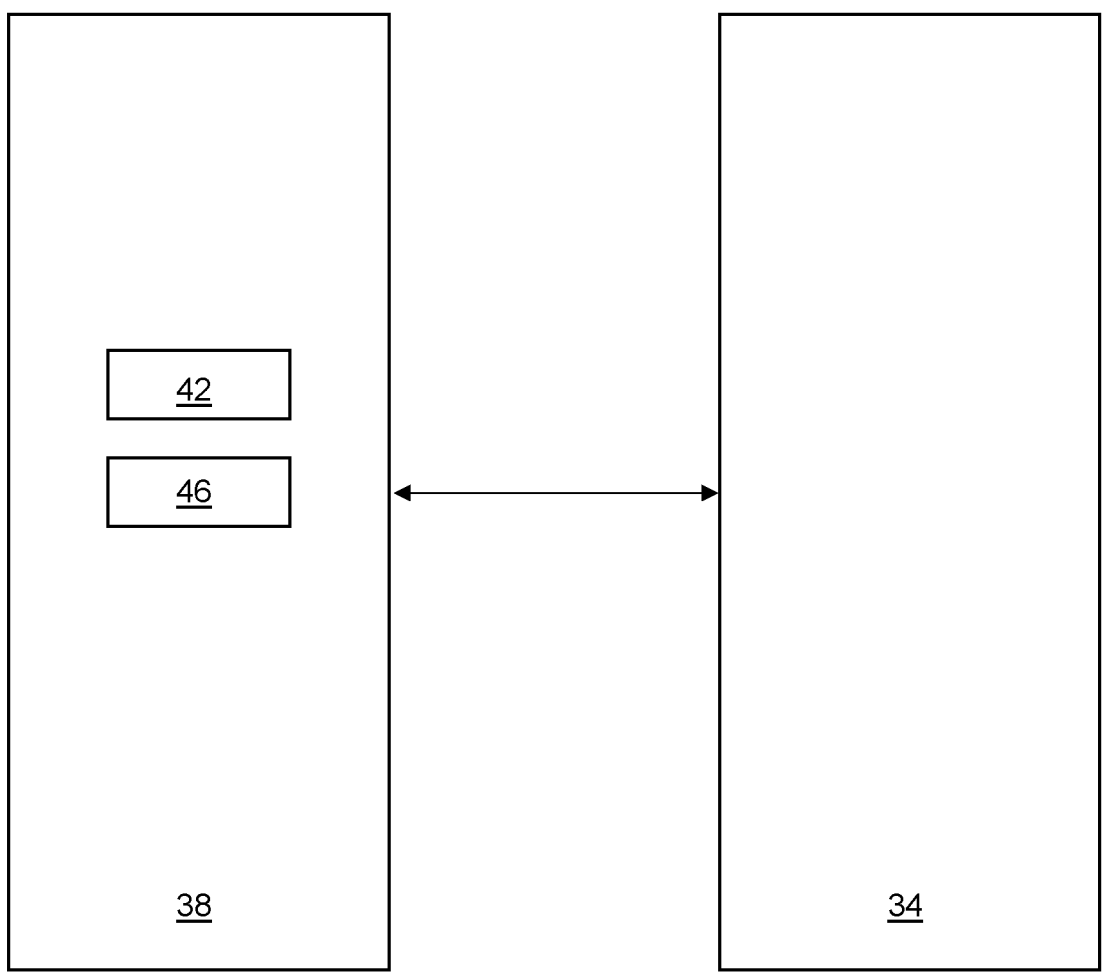
FIG. 2 is a schematic of a system that can be used to perform some of the present methods.

Referring to FIGS. 1 and 2, shown is an illustrative method 10 for analyzing a central nervous system of a patient and a system 30 configured to perform method 10. System 30 can include a processing device (e.g., 38) having one or more processors configured to perform the actions described below. The processing device can be a part of a computer system including standard components such as a hard drive, monitor, printer, keyboard, and mouse, and/or the like that may enable a user to interact with the processing device. The processor(s) thereof can communicate with a memory source and/or non-transitory computer readable medium to receive one or more instructions enabling the process(s) to perform the actions described below, and in some methods can be actively be performing those actions based on one or more instructions received from the memory source and/or non-transitory computer readable medium. While some of the present methods are described with reference to system 30, system 30 is not limiting on those methods, which can be performed with any suitable system.

Figure 3:
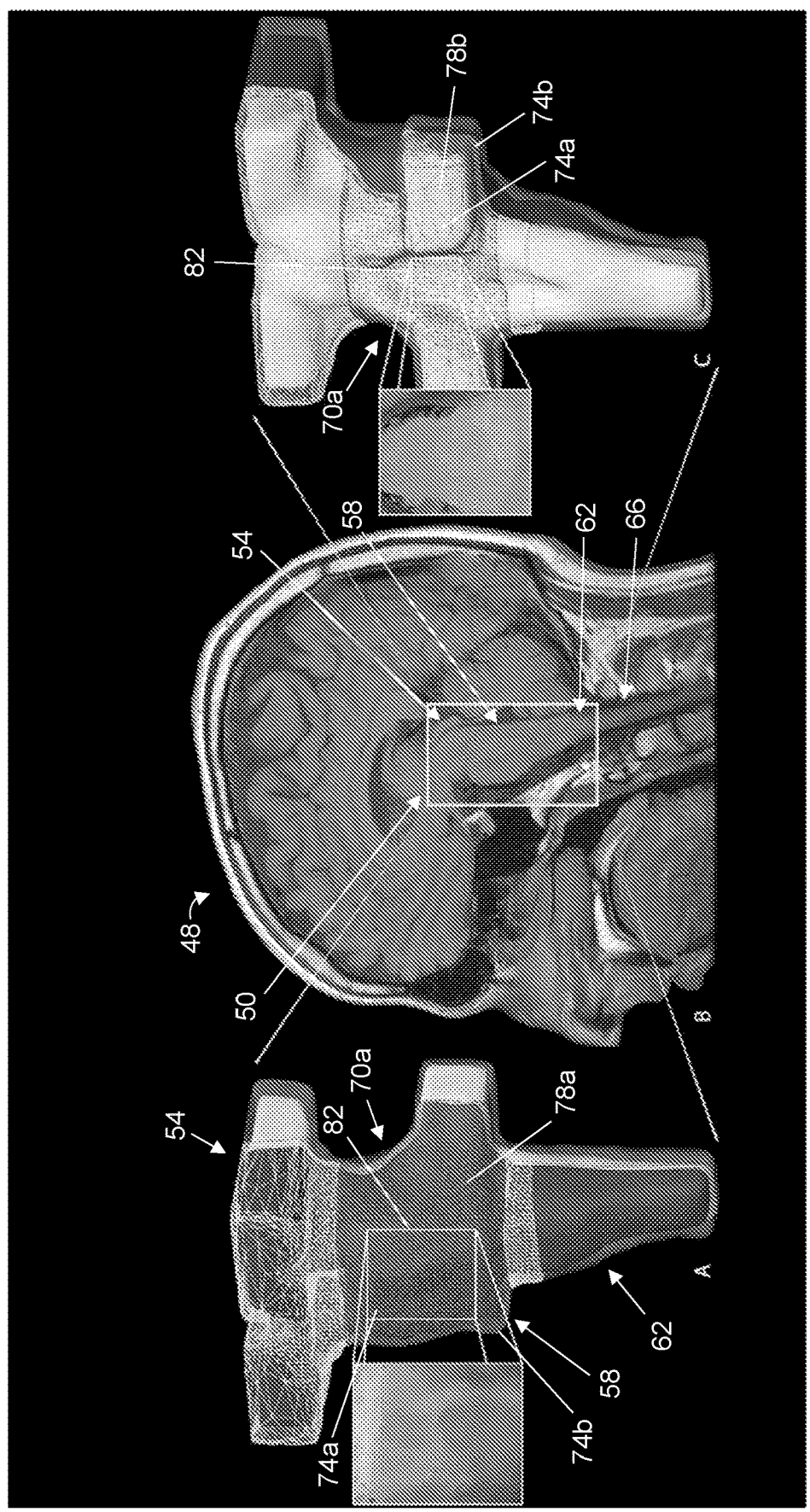
FIG. 3 includes (1) an MRI image showing a patient's brain and upper cervical spinal cord with the brainstem outlined (middle), and (2) ventral and dorsal views (left and right, respectively) of 3D representations of the brainstem segmented into ventral and dorsal portions. Each of the views of the 3D representations include a 3D representation of the brainstem at a first time (solid) and a 3D representation of the brainstem at a second time that is after the first time (mesh).

Referring additionally to FIG. 3, some methods comprise a step 14 of obtaining data that includes, for each of one or more sections (e.g., 70a) of the central nervous system (e.g., 48) of the patient, one or more 3D representations (e.g., 74a and 74b) of the section. Each of the 3D representation(s) can be segmented from a 3D MRI image (e.g., a T1-weighted or a T2-weighted 3D MRI image) or a plurality of 2D MRI images that together can form a 3D representation of the imaged area (e.g., by stitching the images together). The MRI image(s) can be obtained with an MRI device (e.g., 34) of system 30, the processor(s) of the system's processing device can be configured to receive each of those image(s), and the system can include a segmentation application (e.g., 42) by which the processor(s) can segment them into one or more regions of interest (ROIs) that can each correspond to one of the section(s). An illustrative segmentation application is OsiriX from Pixmeo SARL of Geneva, Switzerland or Materialise Mimics from Materialise NV, Leuven, Belgium.

Each of the 3D representation(s) of a section can comprise data that represents the geometry of the section (e.g., from which the volume, surface area, and/or mean curvature thereof can be calculated as described below). For example, each of the 3D representation(s) can represent the section as a polyhedron whose surface is defined by a plurality of polygons (e.g., triangles) and include data regarding the position of the polygons' vertices in 3D coordinates (e.g., 3D Cartesian coordinates) and/or the polygons' unit normals. As an illustration, the 3D representation(s) can each be a stereolithography (.stl) file representing the surface geometry of the section. FIG. 3 illustrates such 3D representations: it includes ventral and dorsal views of 3D representations of a brainstem (e.g., 50) to the left and right, respectively, of the MRI image, each of the views including a first 3D representation (e.g., 74a) of the brainstem at a first time and a second 3D representation (e.g., 74b) of the brainstem at a second time that are superimposed on one another, with each of the representations comprising a polyhedron. In other embodiments, however, for each of the section(s), the 3D representation(s) thereof can include any suitable data representing the geometry of the section.

Each of the section(s) can include at least a portion of the patient's brainstem, such as the midbrain (e.g., 54), pons (e.g., 58), and/or medulla (e.g., 62), and, optionally, at least a portion of the upper cervical spinal cord (e.g., 66). As described in further detail below, the section(s) can include a first section (e.g., 70a) that comprises the pons (FIG. 3) and/or a second section (e.g., 70b) that comprises the medulla and upper cervical spinal cord (FIGS. 5A-5C), the analysis of which can facilitate the diagnosis and assessment of neurological diseases such as MS.

Some methods include a step 18 of segmenting each of the 3D representation(s) of each of the section(s) into ventral (e.g., 78a) and dorsal (e.g., 78b) portions. The ventral and dorsal portions can be segmented through a vertical dissection, with the ventral and dorsal portions each having a volume that is greater than or equal to any one of, or between any two of, 30%, 40%, 50%, 60%, or 70% (e.g., between 40% and 60%) of the volume of the section. For example, a surface can separate the ventral and dorsal portions such that, along a path that extends from the top of the section to the bottom of the section along the surface to bisect the surface, a horizontal distance between the path and the ventral portion's surface is within 10% of a horizontal distance between the path and dorsal portion's surface.

One or more geometric characteristics of each of the section(s) can be assessed. To do so, the processing system can include a 3D imaging application (e.g., 46) by which the processor(s) can calculate the section characteristics from the data including 3D representation(s) thereof.

Figure 4:
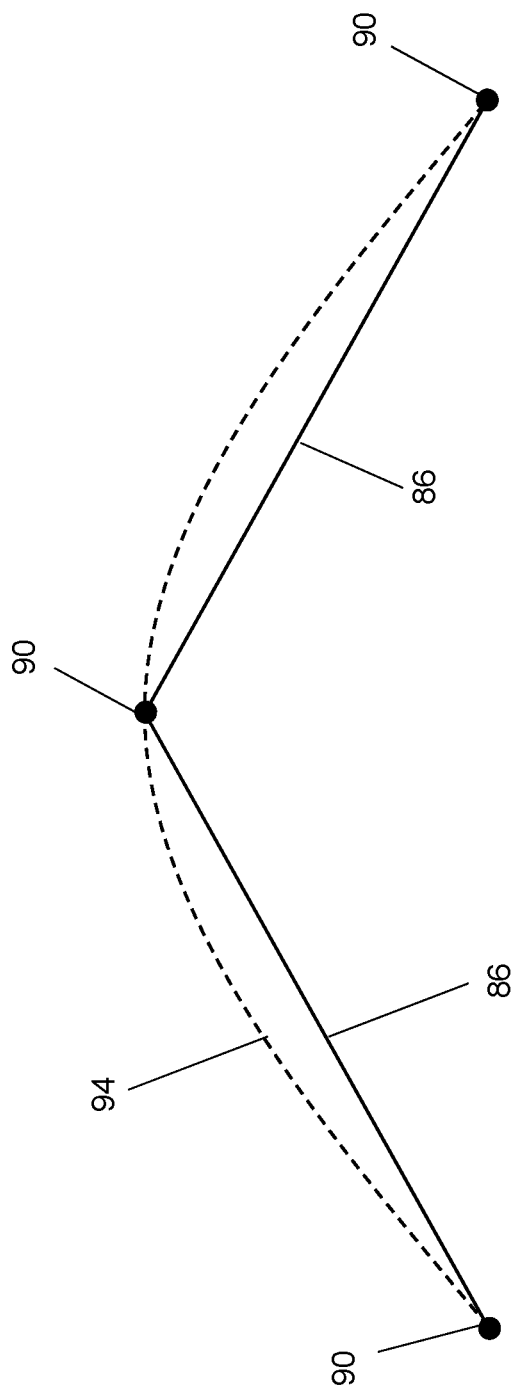
FIG. 4 illustrates one approach for determining the mean curvature of a 3D representation of a section of the central nervous system.

Some methods comprise a step 22 of determining, for at least one—up to and including each—of the 3D representation(s) of each of the section(s), a mean curvature of at least a region (e.g., 82) of the dorsal portion's surface and/or a mean curvature of at least a region of the ventral portion's surface. The mean curvature can be determined in any suitable manner. Referring to FIG. 4, when the 3D representation comprises a polyhedron having a plurality of polygonal (e.g., triangular) faces (e.g., 86), determining the mean curvature of a region of the surface can comprise calculating a curvature of each of the region's polygonal faces and averaging them. To calculate the curvature of each polygonal face, a curvature can be determined for each vertex (e.g., 90) thereof using, for example, paraboloid fitting (e.g., with least squared residuals) or quadric fitting of a curved surface (e.g., 94) to the surface of the 3D representation around the vertex. Curvature calculations can also be based on Gaussian curvature and the Gauss-Bonnet theorem of angle deficit. A curvature of the fitted curve (e.g., a maximum curvature thereof) can be assigned to the vertex, and the face's curvature can be calculated as the average of the curvatures of its vertices. A positive curvature is convex, while a negative curvature is concave. An illustrative program for determining a region's mean curvature is the Materialise Mimics Curvature Analysis tool.

For each of the ventral and/or dorsal portions of a section, a planform area of the region of the surface subject to curvature analysis can be greater than or equal to any one of, or between any two of, 20, 30 40, 50, 60, 70, 80, 90, 100, 150, 200, 250, 300, 350, 400, or 450 square millimeters (mm$^2$). The region of the surface subject to curvature analysis can also be positioned centrally on the ventral or dorsal portion, e.g., such that a sagittal plane and/or a transverse plane intersecting a centroid of the section also intersects the region of the surface being analyzed.

The rate at which mean curvature changes can also be assessed. For example, for each of the section(s) of the central nervous system analyzed, the one or more 3D representations thereof can include a first 3D representation of the section at a first time and a second 3D representation of the section at a second time that is after the first time (e.g., from one or more MRI images taken at the first time and one or more MRI images taken at the second time). For each of the ventral and/or dorsal portions, the mean curvature of the region of the surface thereof can be determined at each of the first and second times and, from that, the rate at which the mean curvature changed from the first time to the second time can be determined. Any suitable time can be elapsed between the first and second times; for example, the time elapsed between the first and second times can be greater than or equal to any one of, or between any two of, 3 months, 4 months, 5 months, 6 months, 1 year, 2 years, 3 years, 4 years, or 5 years (e.g., between 6 months and 5 years).

The volume and surface area of the brain (or portions thereof, such as the brainstem or one or more of the brainstem components (midbrain, pons, and/or medulla)) and/or the upper cervical spinal cord can be determined from the data, as can the rate of change thereof from the first time to the second time. Such volume and surface area calculations can also be performed for each of the ventral and dorsal portions of each of the section(s). When each of the 3D representations comprises a polyhedron, a change in volume can be calculated by, for each of the polygonal faces of the polyhedron, determining a distance between a centroid of the face at the first time and a surface of the face at the second time (e.g., to determine the distance the face moved) and multiplying the surface area of the face at the first time by the distance. The change in volume can be the sum of the products of the faces, and the rate of change can be determined by dividing the volume change by the time elapsed between the first and second times. In other embodiments, however, the rate of change in volume can be determined in any suitable manner.

The determination of geometric characteristic(s) of the central nervous system can be used at least in part to characterize the presence of, the state of, and/or an efficacy of a treatment for a neurological disease in the patient, optionally in view of the patient's ethnicity. Ethnicity information relevant to the disease characterization can include whether the patient is Black (e.g., of African descent, such as an African American) or white (e.g., of European descent). The processor(s) can be configured to perform the determination of geometric characteristic(s) and the disease and/or treatment characterization.

For example, some methods comprise a step 26 of characterizing whether the patient has MS and/or the type of MS in the patient based at least in part on the geometric characteristic(s). Characterizing the type of MS in a patient can include determining whether MS is non-progressive (e.g., relapsing-remitting MS, such as when the patient's Expanded Disability Status Scale (EDSS) is less than 3.0, including 0.0) or progressive (e.g., primary progressive, secondary progressive, or progressive-relapsing MS, such as when the patient's EDSS is greater than or equal to 3.0). The geometric characteristic(s) can also be informative regarding MS severity in each of these disease courses, such as the risk of a non-progressive MS patient entering a progressive MS disease course.

Some methods can also be performed to assess the efficacy of a treatment based on the geometric characteristic(s); in such methods, the treatment (e.g., a medication) can be administered to the patient (e.g., between the first and second times), where a determination that MS is not progressing may indicate that the treatment is effective while a determination that MS is progressing may indicate that it is not. This assessment of treatment efficacy can be used for trials analyzing the efficacy of new treatments, or to determine whether a different treatment should be used (e.g., when the initial treatment is ineffective). Illustrative MS treatments whose efficacy can be assessed include beta interferons, glatiramer, siponimod, dimethyl fumarate, alemtuzumab, plasma exchange, and/or the like.

As described above, a first one of the section(s) of the central nervous system analyzed can include the patient's pons. Segmentation of the first section into ventral and dorsal portions and determining a mean curvature of a region of the surface of at least one of the portions can facilitate the diagnosis and assessment of neurological diseases such as MS. For example, for a region of the surface of the first section's ventral portion (e.g., having a planform area that is between 100 and 450 $mm^2$), the mean curvature thereof can be different for (in decreasing order) healthy patients, white non-progressive MS patients, Black non-progressive MS patients, white progressive MS patients, and Black progressive MS patients, with healthy and non-progressive white MS patients tending to exhibit convex mean curvatures (i.e., that are greater than 0) and the other cohorts tending to exhibit concave mean curvatures (i.e., that are less than 0). As such, an MS diagnosis can be supported by a determination that the mean curvature of the region of the first section's ventral portion is less than or equal to any one of, or between any two of, 0, −0.1, −0.2, −0.3, −0.4, or −0.5 mm (e.g., less than or equal to 0 mm), even for Black patients not exhibiting clinical symptoms of MS (e.g., with an EDSS score of 0.0). This can include a determination that the patient has progressive MS when, for example, the mean curvature of the region of the surface of the ventral portion is less than or equal to −2.0 mm. Furthermore, the assessment can include a determination of whether the ventral mean curvature falls within at least one of five or more ranges, including a first range of between 0.10 and 0.40 mm (e.g., indicating similarity to healthy patients), a second range of between 0 and 0.60 mm (e.g., indicating similarity to white non-progressive MS patients), a third range of between −1.25 and 0.10 mm (e.g., indicating similarity to Black non-progressive MS patients), a fourth range of between −4.5 and −2.0 mm (e.g., indicating similarity to white progressive MS patients), and fifth range of between −8.0 and −5.0 mm (e.g., indicating similarity to Black progressive MS patients). A determination of whether a mean curvature falls within a range can include a determination of whether the mean curvature falls within a sub-range within the range.

The mean curvature of a region of the surface of the first section's dorsal portion (e.g., having a planform area that is between 20 and 70 $mm^2$) can also be informative in the MS assessment, with white non-progressive MS patients tending to have a baseline mean curvature in the region of the dorsal portion's surface that is concave and similar to that of healthy patients and the other cohorts tending to have mean curvatures that are closer to zero. For example, a mean curvature in the region of the dorsal portion's surface that is greater than or equal to any one of, or between any two of, −2.0, −1.75, −1.50, −1.25, or −1.00 mm (e.g., greater than or equal to −1.00 mm) can support a diagnosis of MS (including a progressive MS diagnosis or, for Black patients with an EDSS less than 3.0, such as 0.0, a non-progressive MS diagnosis), and a determination that the dorsal mean curvature is less than −1.0 mm can support a non-progressive MS determination (e.g., for white patients).

Rates of change in the mean curvature of the region of the ventral portion and/or the region of the dorsal portion of the first section can also be informative in the MS and/or treatment characterization. In the region of the dorsal portion subject to curvature analysis, the rate of change in the mean curvature thereof from the first time to the second time can be larger (e.g., with a faster shift toward convexity) for non-progressive white MS patients than for other cohorts, and can be larger for Black progressive MS patients than for Black non-progressive MS. When the patient is white, a determination that the rate of change in the mean curvature is greater than or equal to any one of, or between any two of, 0.65, 0.70, 0.75, 0.80, 0.85, or 0.90 mm/year (e.g., greater than or equal to 0.65 mm/year) can support a characterization that the patient has non-progressive MS. When the patient is Black, a determination that the rate of change in the mean curvature is less than or equal to any one of, or between any two of, 0.40, 0.38, 0.36, 0.34, 0.32, 0.30, or 0.28 mm/year (e.g., between 0.25 and 0.40 mm) can support a characterization that the patient has non-progressive MS. This rate-of-change assessment can also be informative of the risk of non-progressive MS patients entering a progressive disease course and/or in the assessment of treatment efficacy. For example, the dorsal rate of change can be compared to a baseline rate of change (e.g., a median rate of range of a cohort the patient belongs to), with rates larger than the baseline indicative of a higher risk of disease progression and/or treatment inefficacy and rates of change lower than the baseline indicative of a lower risk of disease progression and/or treatment efficacy.

In the region of the ventral portion of the first section subject to curvature analysis, non-progressive MS patients may tend to exhibit rates of change in mean curvature from the first time to the second time that are higher than (e.g., with a slower shift toward concavity) those of progressive MS patients. For example, a determination that the rate of change in the mean curvature of the region of the first section's ventral portion is greater than or equal to any one of, or between any two of, −0.60, −0.50, −0.40, −0.30, or −0.20 mm/year (e.g., greater than or equal to −0.50 mm/year) can support a determination that the patient has non-progressive MS. The ventral rates may also be informative of the risk of disease progression and/or treatment efficacy and, as with the dorsal rate of change, can be compared to a baseline rate of change, with faster rates toward concavity (e.g., lower than the baseline) indicative of a higher risk of progression and/or an ineffective treatment and slower rates toward concavity (e.g., above the baseline) indicative of a lower risk of progression and/or effective treatment.

Figure 5A:
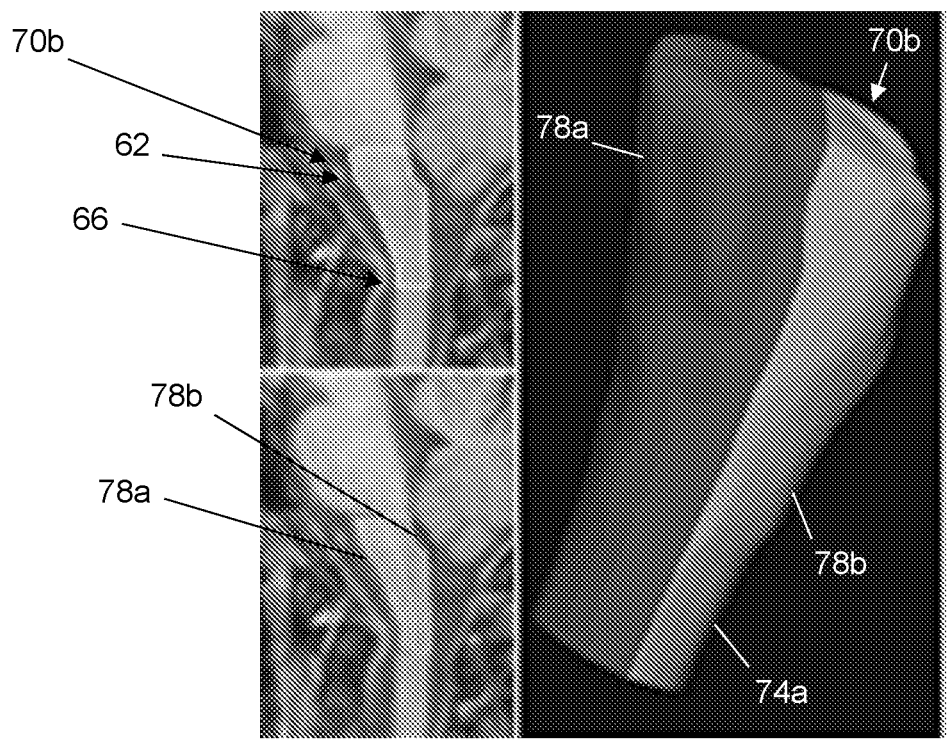
FIGS. 5A and 5B each show an MRI image of a section of the central nervous system that includes the medulla and upper cervical spinal cord (upper left), segmentation of the section (lower right), and a 3D representation of the segmented section (right) at first and second times, respectively.
Figure 5B:
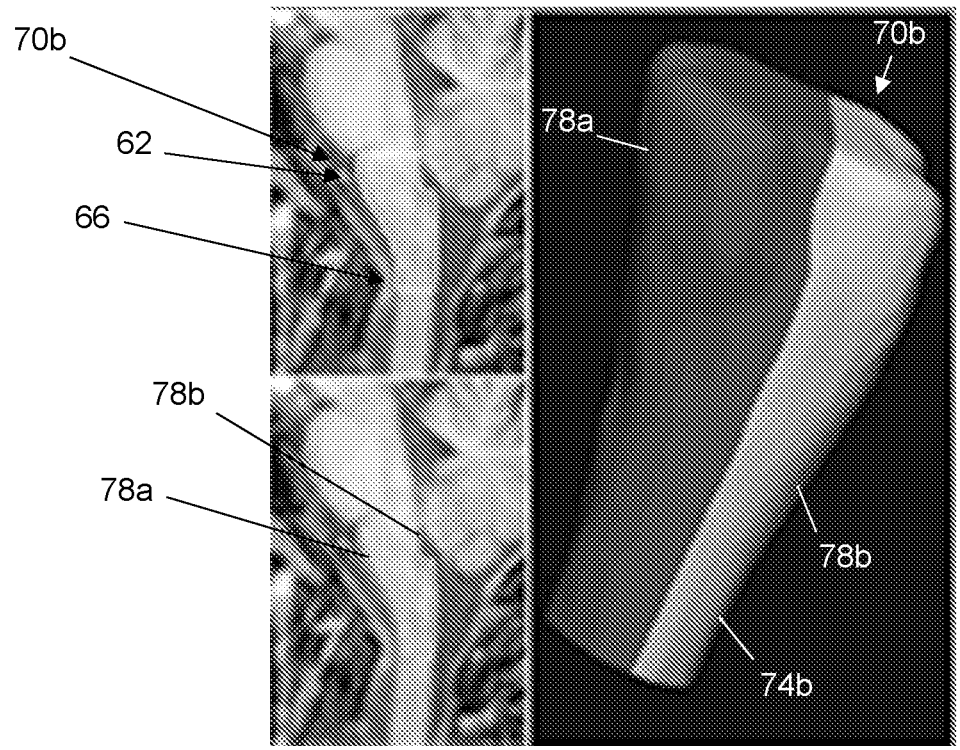
Figure 5C:
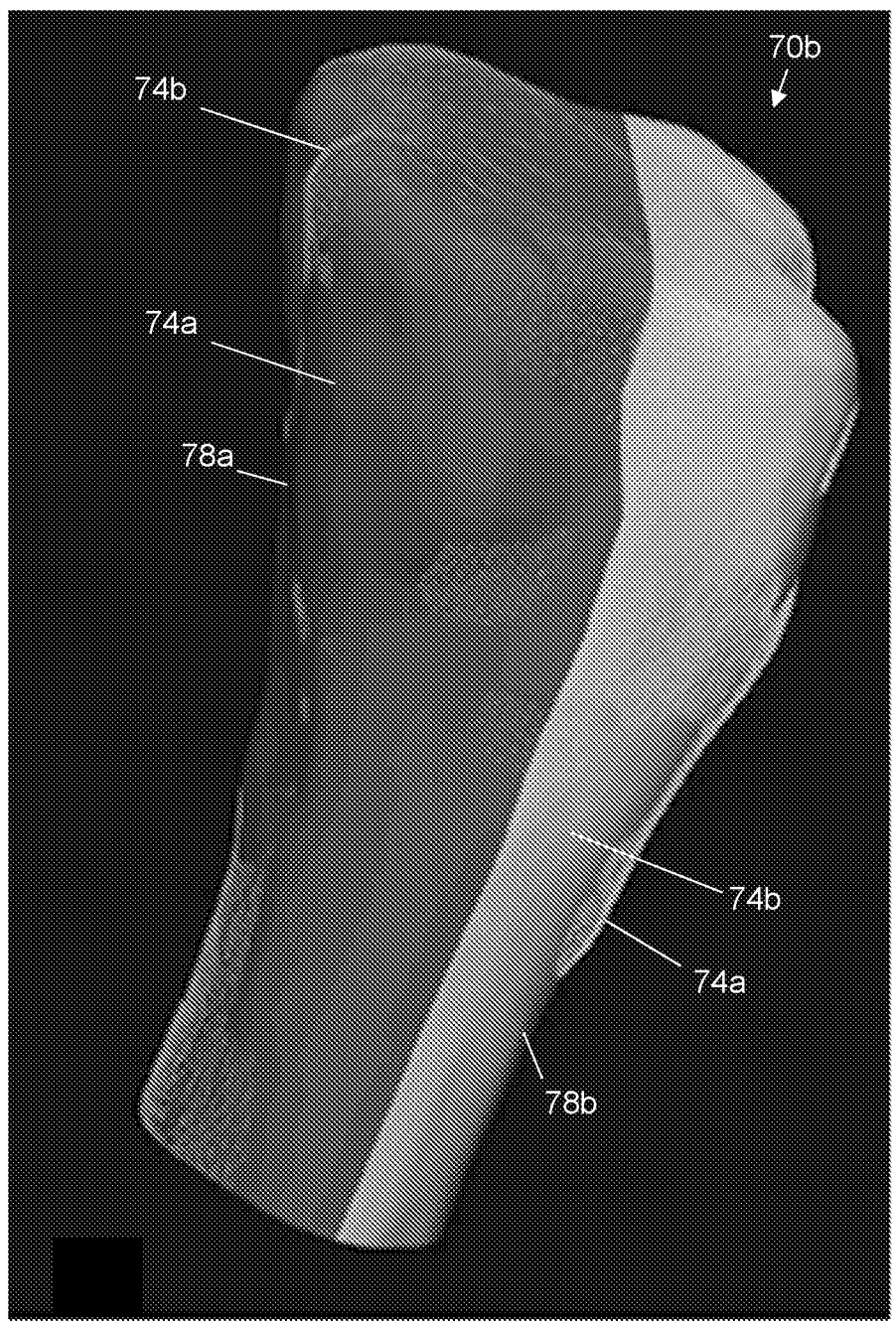
FIG. 5C shows 3D representations of the section of FIGS. 5A and 5B at the first and second times (solid and mesh, respectively) superimposed on one another.

Referring additionally to FIGS. 5A-5C, as described above a second one of the section(s) can include the patient's medulla and upper cervical spinal cord, and determining the mean curvature of a region of its dorsal portion (e.g., having a planform area that is between 40 and 85 mm²) can also facilitate the MS characterization. For example, for that region of the dorsal portion, Black non-progressive MS patients can exhibit a baseline mean curvature that is convex but has a lower rate of change (e.g., can be a higher rate toward concavity) when compared to non-progressive white MS patients and healthy patients. As such, a determination that the mean curvature of that region is greater than or equal to any one of, or between any two of, 0.0, 0.25, 0.50, 0.75, 1.00, 1.25, 1.50, 1.75, 2.00, 2.25, 2.50, 2.75, or 3.00 mm (e.g., greater than or equal to 1.00 mm) and/or that the rate of change thereof is less than or equal to any one of, or between any two of, −0.50, −1.00, −1.50, −2.00, −2.50, −3.00, or −3.50 mm/year (e.g., less than or equal to −1.50 mm/year) can support a non-progressive MS characterization when the patient is Black. And as with the first section, the rates of change in dorsal mean curvature in the second section can be informative of the risk of disease progression and/or treatment efficacy and can be compared to a baseline rate of change, with faster rates toward concavity (e.g., lower than the baseline) indicative of a higher risk of progression and/or an ineffective treatment and slower rates toward concavity (e.g., higher than the baseline) indicative of a lower risk of progression and/or an effective treatment.

The volume and/or surface area determinations described above can also facilitate the characterization of a neurological disease such as MS. For example, in the brainstem, each of the brainstem components, and/or the upper cervical spinal cord (including in each of the ventral and dorsal portions thereof), while healthy patients and white non-progressive MS patients can each exhibit volume and/or surface area increases, Black non-progressive MS patients—like progressive MS patients—can exhibit volume and/or surface area reductions in those portions of the central nervous system. A determination that the rate of change in volume and/or surface area of the brainstem, one or more of its components, the upper cervical spinal cord, and/or ventral and dorsal portions thereof is less than or equal to 0.0 mm³/year and less than or equal to 0.0 mm²/year, respectively, can support a diagnosis of MS, including a characterization that the patient has non-progressive MS when the patient is Black.

Because neurological diseases like MS may affect the central nervous systems of different patients differently, each of the above-described characterizations can be made without satisfaction of all criteria supporting the characterization (e.g., a diagnosis can be based on the curvature analysis of the first section alone or of the second section alone). When multiple sections are analyzed, determining geometric characteristics of each of the sections and assessing at least one of the curvature-, volume-, and surface-area-based criteria based on those characteristics can facilitate a more accurate characterization of the presence and/or stage of a neurological disease such as MS. This is particularly so with the curvature analysis and segmentation of each of the section(s) into ventral and dorsal portions, which as set forth above provide reliable metrics through which disease states can be identified and neurological decline can be projected in a wide range of patients, including in patients having different ethnicities. This in turn can permit more personalized assessments than prior metrics.

EXAMPLES

Aspects of the present invention will be described in greater detail by way of specific examples. The follow examples are offered for illustrative purposes only and are not intended to limit the invention in any manner. Those of skill in the art will readily recognize a variety of noncritical parameters that can be changed or modified to yield essentially the same results.

Example 1

The brainstems of 50 patients were analyzed using 3D MRI. The patients were placed in four MS groups and a healthy control group with no history of brain anomalies typical for central nervous system demyelination based on the observed radiological features and formal imaging interpretations by board certified neuroradiologists and clinical impressions by specialists in MS. For each of the MS groups, the patients had a confirmed diagnosis of MS based on established criteria, results from supporting para-clinical studies (i.e., cerebrospinal fluid profiles, electrophysiological data, serological results), and the exclusion of other disease states. First and second ones of the MS groups each comprised African American patients, the first group being patients who had an EDSS score of 0.0 (representing the non-progressive relapsing-remitting group) and the second group being patients who had an EDSS score that was greater than 6.0 who initially experienced a relapsing course, and later developed a progressive disease course (representing the progressive MS group). Third and fourth ones of the MS groups each comprised white patients, the third group being a non-progressive MS group (EDSS score of 0.0) and the fourth group being a progressive MS group (EDSS score that was greater than 6.0).

All imaging studies were performed on a 3T MRI scanner (Achieva, Philips Medical Systems, Cleveland, OH) using a 32-channel phased array head coil for reception and the built-in scanner body coil for transmission. Each MRI study included scout localizers, 3D high-resolution magnetization prepared rapid gradient echo (MPRAGE) T1-weighted isotropic ($1.1 \times 1.1 \times 1.1$ mm$^3$, TE/TR/TI=3.7/8.1/864 ms, flip angle 12 degrees, $256 \times 220 \times 170$ mm$^3$ FOV, number of excitations (NEX)=1, 170 slices, duration: 4:11 min), 3D fluid-attenuated inversion recovery (FLAIR) ($1.1 \times 1.1 \times 1.1$ mm$^3$, TE/TR/TI=350/4800/1600 ms, flip angle 90 degrees, $250 \times 250 \times 180$ mm$^3$ FOV, NEX=1, 163 slices, duration: 5:02 min), and 3D T2-weighted turbo spin echo sequence acquired in the sagittal plane ($1.0 \times 1.0 \times 1.0$ mm$^3$, TE/TR/T229/2500/1600 ms, flip angle 90 degrees, $250 \times 250 \times 180$ mm$^3$ FOV, NEX=1, 164 slices, duration: 4:33 min).

The MRI images were segmented and analyzed without knowledge of demographic data, clinical history, current or past treatments, or disease duration. MRI registration was initially performed based on structural positioning and intensity using an in-house software package (Med-IP, which was used in prior studies, such as in Sivakolundu et al., *BOLD signal within and around white matter lesions distinguishes multiple sclerosis and non-specific white matter disease: a three dimensional approach*, J. Neurol. 2020) and were aligned using the Insight Toolkit (ITK) (version 5.1.1; Kitware Clifton Park, N.Y., U.S.A.), and multi-resolution rigid registration was performed with Mattes Mutual Information Metric. To ensure proper intensity alignment, histogram matching of intensities involving regions of interest through linear transforms and ordered correspondence on a set of match points computed from the quantiles of each histogram were performed.

The region of interest—at least a portion of the brainstem—isolated from the 3D T1-weighted MRI images had a craniocaudal dimension of 50 mm from the superior colliculus of the midbrain to the caudal end of the medulla. This region of interest was isolated using Materialise Mimics (version 22.0; Materialise NV, Leuven, Belgium). For each patient, the 3D representation of the brainstem was obtained at a first time and at a second time that was after the first time. Masks were generated from both MRI time points. Additionally, each 3D representation of the brainstem was segmented into ventral and dorsal portions based on centroid measures, and into portions isolating the midbrain, pons, and medulla. Materialise 3-matic (version 14.0, Materialise NV, Leuven, Belgium) was used to enhance the segmented isolated regions of interest.

For each patient and at each time point, the volume and surface area of the brainstem, each of its components, and the ventral and dorsal portions thereof were determined. Temporal changes in volume and surface area were also determined. To measure volume changes, for each polygonal face of the polyhedron representing the brainstem, the distance from the centroid of the face at the first time to the surface of the polygon at the second time (using co-registered images) was determined and multiplied by the surface area of the face. The change in volume was calculated as the sum of the products of every face.

Furthermore, normalized whole brain, T2-weighted lesion, cortical grey matter, and thalamic volumes were determined by applying the icobrain pipeline (Icometrix, Leuven, Belgium) to the 3D T1-weighted and FLAIR images. After bias field correction and skull stripping, the FLAIR and T1-weighted images were co-registered and segmented into different classes: grey matter, white matter, cerebrospinal fluid, and T2-weighted lesions related to MS. Normalized whole brain, T-2 weighted lesion, and cortical grey matter volumes were then calculated therefrom. Thalamic volumes were computed based on the 3D T1-weighted and FLAIR images using multi-atlas registration followed by label fusion and level-set optimization. Subsequently, a Jacobian integration approach was performed, based on the segmentations of each individual time point, providing the percentage brain volume change between time points as well as the final volumetric measurements for whole brain, cortical grey matter, and thalamus. Normalization was performed for head size. Temporal changes in lesion volume were obtained by simultaneously evaluating the lesion maps of the individual time points.

For each patient, mean curvature (surface complexity) was also calculated for a 18.5 mm×9 mm×20 mm region at the ventral portion of the pons and for a 7.5 mm×4 mm×7.5 mm region at the dorsal portion of the pons at the first and second times. Within each of the regions, the mean curvature was determined using maximum curvature analysis, which provided the local maximum curvature for each triangle and vertex of the 3D representation. The maximum curvature analysis was performed using Med-IP and confirmed with Materialise Mimics (version 22.0, Materialise NV, Leuven, Belgium). Zero represented a baseline for determining the degree of change between time points, with negative mean values indicating a more concave surface and positive mean values reflecting a more convex surface.

Figure 6:
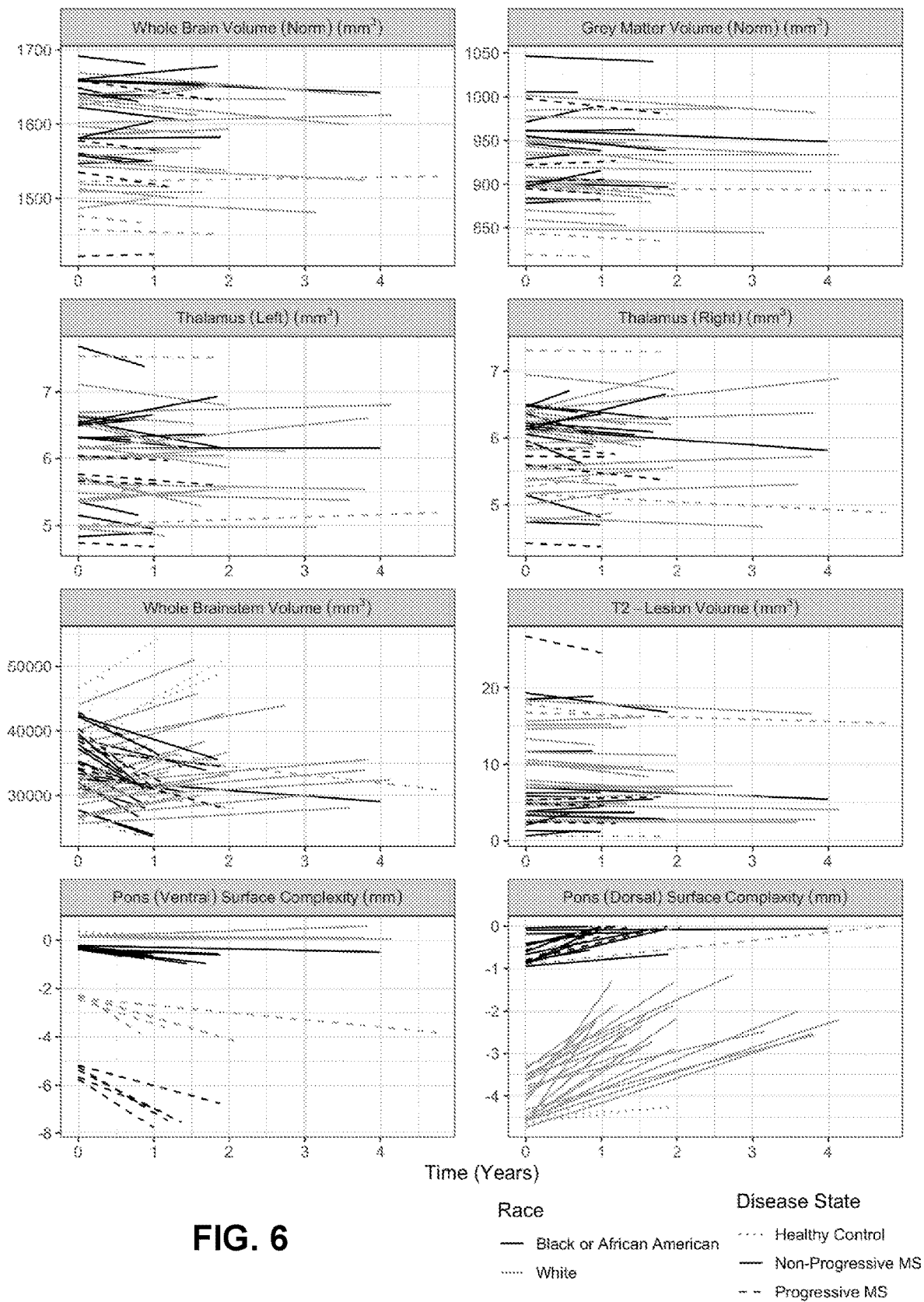
FIG. 6 is a set of graphs showing normalized whole brain volume, normalized grey matter volume, left thalamus volume, right thalamus volume, whole brainstem volume, T2 lesion volume, mean curvature (surface complexity) of a region of the pons's ventral portion, and mean curvature (surface complexity) of a region of the pons's dorsal portion over time for healthy, non-progressive MS, and progressive MS patients that were African American and white.
Figure 7A:
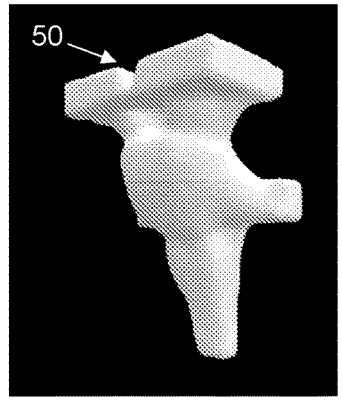
FIGS. 7A-7C are 3D representations of a brainstem of a healthy patient, with FIGS. 7B and 7C showing ventral and dorsal views, respectively, thereof.
Figure 7B:
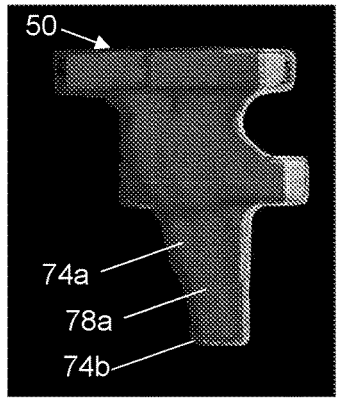
Figure 7C:
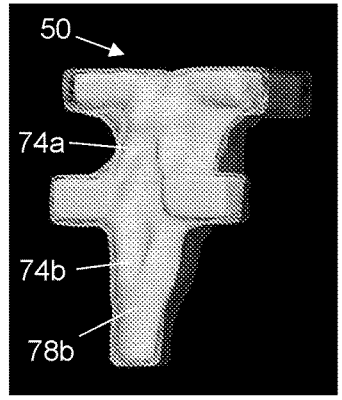
Figure 8A:
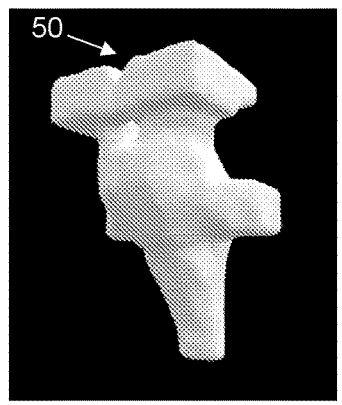
FIGS. 8A-8C are 3D representations of a brainstem of an African American patient with non-progressive MS, with FIGS. 8B and 8C showing ventral and dorsal views, respectively, thereof.
Figure 8B:
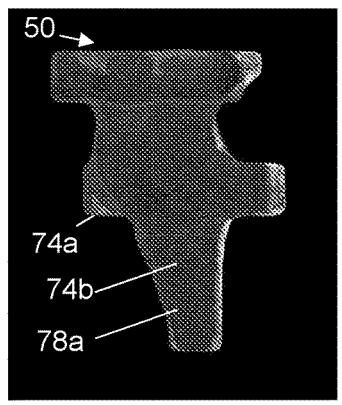
Figure 8C:
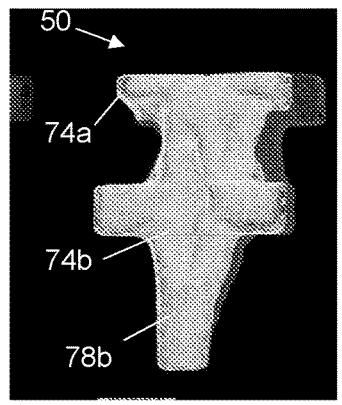
Figure 9A:
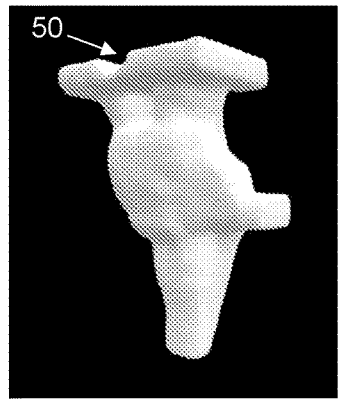
FIGS. 9A-9C are 3D representations of a brainstem of an African American patient with progressive MS, with FIGS. 9B and 9C showing ventral and dorsal views, respectively, thereof.
Figure 9B:
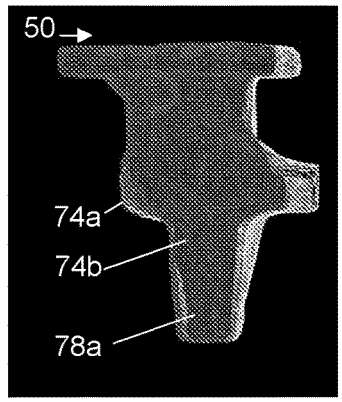
Figure 9C:
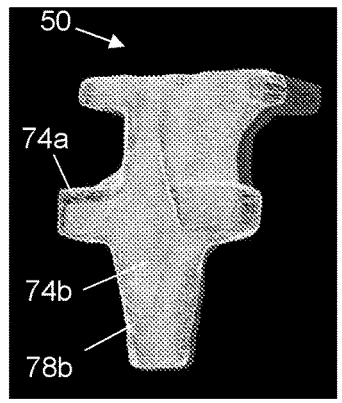
Figure 10A:
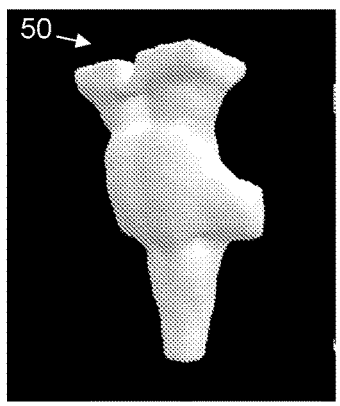
FIGS. 10A-10C are 3D representations of a brainstem of a white patient with non-progressive MS, with FIGS. 10B and 10C showing ventral and dorsal views, respectively, thereof.
Figure 10B:
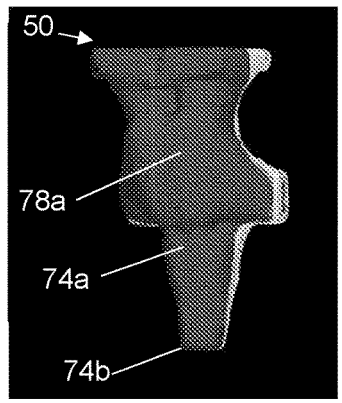
Figure 10C:
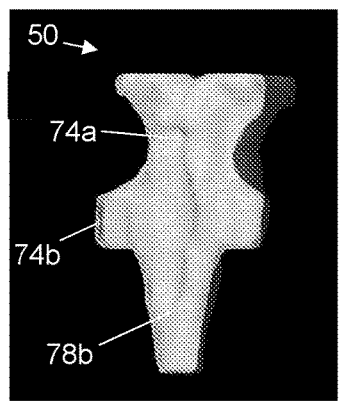
Figure 11A:
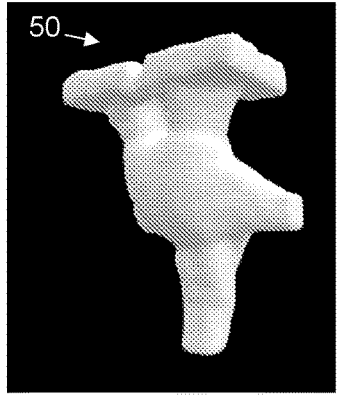
FIGS. 11A-11C are 3D representations of a brainstem of a white patient with progressive MS, with FIGS. 11B and 11C showing ventral and dorsal views, respectively, thereof.
Figure 11B:
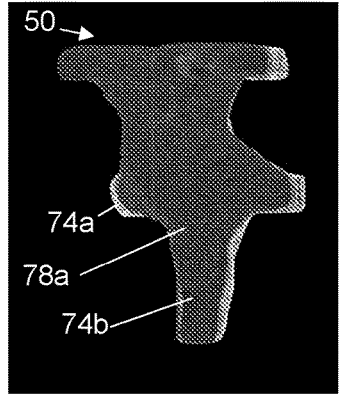
Figure 11C:
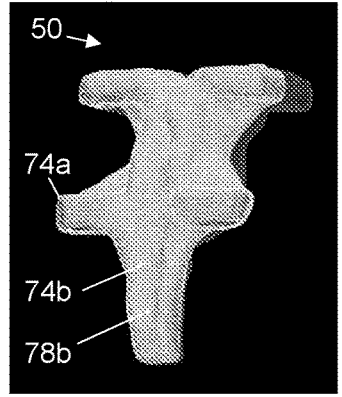

TABLES 1-3, below, set forth the clinical data (e.g., patient characteristics) and geometric data—such as volume, surface area, and mean curvature (surface complexity)—of the portions of the central nervous system that were analyzed for healthy, African American, and white patients, respectively. TABLE 4, below, sets forth the p-values reflecting the level of significance of differences between certain cohorts. A p-value of less than 0.05 was considered statistically significant. FIG. 6 also includes graphs showing geometric characteristics of the analyzed portions of the brainstem.

TABLE 1

Clinical and Geometric Data for Healthy Patients

| | | | |
|---|---|---|---|
| Subjects | | | 5 |
| Median Age (Range) | | | 51.75 (38.79-61.46) |
| Female (%) | | | 2 (40%) |
| Median (Range) Rate of Volume Change (mm³/year) | Grey Matter | | — |
| | Left Thalamus | | — |
| | Right Thalamus | | — |
| | T2 Lesion | | — |
| Median (Range) % Volume Rate of Change | Whole Brain | | — |
| | Grey Matter | | — |
| Median (Range) 3D Atrophy (mm³) | Brainstem | Ventral | 0 (0-39.67) |
| | | Dorsal | 0 (0-6.62) |
| | Midbrain | Ventral | 0 (0-39.67) |
| | | Dorsal | 0 (0-6.62) |
| | Pons | Ventral | 0 (0-0) |
| | | Dorsal | 0 (0-0) |
| | Medulla | Ventral | 0 (0-0) |
| | | Dorsal | 0 (0-0) |
| Median (Range) Surface Area Rate of Change (mm²/year) | Brainstem | Total | 524.72 (408.61-1912.68) |
| | | Ventral | 270.58 (202.03-821.8) |
| | | Dorsal | 256.27 (206.58-1090.89) |
| | Midbrain | Total | 189.61 (79.68-592.02) |
| | | Ventral | 116.72 (−5.19-205.74) |
| | | Dorsal | 84.87 (26.13-386.28) |
| | Pons | Total | 370.24 (198.28-1567.14) |
| | | Ventral | 175.97 (67.86-597.52) |
| | | Dorsal | 163.72 (130.41-969.62) |
| | Medulla | Total | 29.95 (20.73-202.9) |
| | | Ventral | 23.49 (10.66-117.3) |
| | | Dorsal | 10.87 (6.46-85.6) |
| Median (Range) Pons Surface Complexity (mm) | Ventral | First Time | 0.3255 (0.223-0.3576) |
| | | Second Time | 0.1725 (0.1253-0.1813) |
| | Dorsal | First Time | −4.48 (−4.6546-3.2123) |
| | | Second Time | −4.2438 (−4.4613-3.1813) |
| Median (Range) Pons Surface Complexity Rate of Change (mm/year) | Ventral | | −0.1 (−0.51-−0.05) |
| | Dorsal | | 0.21 (0.09-0.31) |

TABLE 2

Clinical and Geometric Data for African American MS Patients

| | | | Non-Progressive | Progressive |
|---|---|---|---|---|
| Subjects | | | 15 | 5 |
| Median Age (Range) | | | 38.15 (22.42-57.84) | 57.01 (41.73-58.02) |
| Female (%) | | | 13 (86.67%) | 4 (80%) |
| Median (Range) Rate of Volume Change (mm³/year) | Grey Matter | | −0.9 (−8.96-18.81), n = 13 | −1.73 (−9.37-4.02), n = 4 |
| | Left Thalamus | | −0.06 (−0.34-0.21), n = 13 | −0.06 (−0.09-−0.05), n = 4 |
| | Right Thalamus | | −0.09 (−0.48-0.43), n = 13 | −0.08 (−0.12-−0.01), n = 4 |
| | T2 Lesion | | 0.06 (−1.35-2.62), n = 13 | −0.17 (−2.18-0.22), n = 4 |
| Median (Range) % Volume Rate of Change | Whole Brain | | −0.24 (−1.38-0.57), n = 11 | −0.88 (−1.09-0.22), n = 3 |
| | Grey Matter | | −0.26 (−0.95-1.92), n = 11 | −0.65 (−0.95-0.43), n = 3 |
| Median (Range) 3D Atrophy (mm³) | Brainstem | Ventral | 2644.48 (1492.63-5647.69) | 4393.48 (2772.98-5659.48) |
| | | Dorsal | 3133.44 (1968.92-5774.37) | 3109.29 (2647.4-5642.12) |
| | Midbrain | Ventral | 1067.07 (264.58-2707.58) | 1559.48 (645.54-3435.47) |
| | | Dorsal | 836.63 (597.3-1481.21) | 1333.08 (914.07-1942.18) |
| | Pons | Ventral | 1151.3 (580.44-3013.79) | 2298.79 (1754.74-3024.78) |
| | | Dorsal | 1839.42 (960.29-4041.85) | 1712.43 (1217.76-3565.97) |
| | Medulla | Ventral | 253.91 (102.14-685.14) | 400.34 (242.36-469.27) |
| | | Dorsal | 296.66 (187.7-591.57) | 161.5 (96.55-326.85) |
| Median (Range) Surface Area Rate of Change (mm²/year) | Brainstem | Total | −544.55 (−1023.73-488.56) | −379.64 (−702.21-−294.24) |
| | | Ventral | −188.02 (−424.51-345.75) | −132.79 (−217.75-−111.44) |
| | | Dorsal | −263.7 (−599.22-295) | −246.24 (−484.46-−176.47) |
| | Midbrain | Total | −85.42 (−337.4-605.17) | −91.06 (−161.19-−6.76) |
| | | Ventral | −22.62 (−313.56-327.95) | −21.86 (−91.38-20.49) |
| | | Dorsal | −42.97 (−136.24-404.84) | −69.81 (−99.43-−27.25) |
| | Pons | Total | −222.01 (−604.25-−31.07) | −228.49 (−536.27-−196.8) |
| | | Ventral | −83.57 (−156.6-−18.96) | −101.84 (−168.27-−59.52) |
| | | Dorsal | −161.32 (−447.65-−12.11) | −133.28 (−368-−126.65) |
| | Medulla | Total | −61.68 (−133.61-67.03) | −39.01 (−60.42-−32.55) |
| | | Ventral | −33.03 (−83.8-44.82) | −23.95 (−37.83-−19.92) |
| | | Dorsal | −31.05 (−68.88-22.21) | −15.52 (−25.29-−11.37) |

TABLE 2-continued

Clinical and Geometric Data for African American MS Patients

| | | | Non-Progressive | Progressive |
|---|---|---|---|---|
| Median (Range) Pons Surface Complexity (mm) | Ventral | First Time | −0.3273 (−0.3908--0.2149) | −5.3782 (−5.7549--5.1814) |
| | | Second Time | −0.6454 (−0.9662--0.4888) | −7.4973 (−7.7712--6.752) |
| | Dorsal | First Time | −0.53475 (−0.9449--0.412) | −0.7994 (−0.8378--0.4456) |
| | | Second Time | −0.12705 (−0.6586--0.0106) | −0.0051 (−0.0099--0.0036) |
| Median (Range) Pons Surface Complexity Rate of Change (mm/year) | Ventral | | −0.36 (−0.62--0.07) | −1.59 (−2.02--0.84) |
| | Dorsal | | 0.31 (0.01-0.9) | 0.56 (0.37-0.75) |

TABLE 3

Clinical and Geometric Data for White MS Patients

| | | | Non-Progressive | Progressive |
|---|---|---|---|---|
| Subjects | | | 20 | 5 |
| Median Age (Range) | | | 35.63 (27.9-61.56) | 44.07 (36.62-55.09) |
| Female (%) | | | 10 (50%) | 2 (40%) |
| Median (Range) Rate of Volume Change (mm³/year) | Grey Matter | | −3.55 (−10.21-1.31) | −2.58 (−4.94--0.32), n = 3 |
| | Left Thalamus | | −0.02 (−0.32-0.12) | 0.04 (−0.01-0.27), n = 3 |
| | Right Thalamus | | 0.03 (−0.27-0.3) | −0.01 (−0.06-0.13), n = 3 |
| | T2 Lesion | | −0.21 (−1.17-0.47) | −0.29 (−1.46--0.06), n = 3 |
| Median (Range) % Volume Rate of Change | Whole Brain | | −0.12 (−0.63-0.97) | −0.23 (−0.81-0.09), n = 3 |
| | Grey Matter | | −0.39 (−1.09-0.15) | −0.31 (−0.59--0.07), n = 3 |
| Median (Range) 3D Atrophy (mm³) | Brainstem | Ventral | 23.39 (0-390.62) | 1343.83 (1005.37-4462.91) |
| | | Dorsal | 1.11 (0-436.92) | 2585.83 (1967.05-2925.88) |
| | Midbrain | Ventral | 12.55 (0-139.21) | 603.76 (349.77-764.61) |
| | | Dorsal | 0.42 (0-119.25) | 725 (449.03-943.82) |
| | Pons | Ventral | 0 (0-279.73) | 580.16 (472.8-2810.92) |
| | | Dorsal | 0 (0-274.51) | 1719.83 (1209.84-1855.13) |
| | Medulla | Ventral | 0 (0-91.8) | 182.81 (74.11-887.38) |
| | | Dorsal | 0 (0-43.16) | 174.51 (65.73-372.78) |
| Median (Range) Surface Area Rate of Change (mm²/year) | Brainstem | Total | 257.44 (21.86-629.44) | −185.33 (−394.44--106.25) |
| | | Ventral | 116.23 (7.01-271.35) | −75 (−96.52--17.87) |
| | | Dorsal | 142.52 (14.85-405.84) | −165.37 (−297.92--30.68) |
| | Midbrain | Total | 114.42 (−4.74-293.71) | −19.52 (−99.58--0.05) |
| | | Ventral | 62.98 (−2.81-214.73) | −12 (−44.67-16.8) |
| | | Dorsal | 34.34 (−19.87-146.32) | −12.19 (−88.49-44.62) |
| | Pons | Total | 125.07 (22.11-432.76) | −157.43 (−260.7--57.34) |
| | | Ventral | 36.57 (−5.13-112.1) | −34.01 (−72.32-3.67) |
| | | Dorsal | 101.2 (12.77-320.66) | −117.94 (−188.38--24.96) |
| | Medulla | Total | 22.49 (4.48-65.96) | −24.71 (−81.59--8.38) |
| | | Ventral | 11.44 (3.13-32.33) | −14.42 (−37.89--3.18) |
| | | Dorsal | 10.68 (1.31-33.63) | −10.29 (−43.7--5.2) |
| Median (Range) Pons Surface Complexity (mm) | Ventral | First Time | 0.1653 (0.1407-0.189) | −2.2995 (−2.4615--2.1922) |
| | | Second Time | 0.06565 (0.0522-0.585) | −3.8736 (−4.1667--3.6167) |
| | Dorsal | First Time | −4.0426 (−4.7523--3.299) | −0.853 (−0.9034--0.8058) |
| | | Second Time | −2.2563 (−2.8783--1.1532) | −0.0044 (−0.0082--0.0006) |
| Median (Range) Pons Surface Complexity Rate of Change (mm/year) | Ventral | | −0.06 (−0.1-0.11) | −0.92 (−2.01--0.3) |
| | Dorsal | | 0.9 (0.4-2.61) | 0.49 (0.19-1.02) |

TABLE 4

P-Values Between Groups

| | | NP AA vs. NP White | Healthy vs. NP White | NP White vs. Prog. White | NP AA vs. Prog. AA | Prog. AA vs. Prog. White |
|---|---|---|---|---|---|---|
| Median (Range) Rate of Volume Change (mm³/year) | Grey Matter | 0.03 | — | 0.91 | 0.27 | 0.81 |
| | Left Thalamus | 0.42 | — | 0.15 | 0.98 | 0.10 |
| | Right Thalamus | 0.13 | — | 0.84 | 0.95 | 0.37 |
| | T2 Lesion | 0.04 | — | 0.50 | 0.15 | 0.71 |
| Median (Range) % Volume Rate of Change | Whole Brain | 0.33 | — | 0.80 | 0.98 | 0.86 |
| | Grey Matter | 0.33 | — | 0.95 | 0.24 | 0.72 |

TABLE 4-continued

| | | | P-Values Between Groups | | | | |
|---|---|---|---|---|---|---|---|
| | | | NP AA vs. NP White | Healthy vs. NP White | NP White vs. Prog. White | NP AA vs. Prog. AA | Prog. AA vs. Prog. White |
| Median (Range) 3D Atrophy (mm³) | Brainstem | Ventral | <0.0001 | 0.13 | 0.0005 | 0.47 | 0.004 |
| | | Dorsal | <0.0001 | 0.04 | 0.0007 | 0.32 | 0.23 |
| | Midbrain | Ventral | <0.0001 | 0.41 | 0.0003 | 0.74 | 0.03 |
| | | Dorsal | <0.0001 | 0.04 | 0.0005 | 0.94 | 0.04 |
| | Pons | Ventral | <0.0001 | 0.07 | 0.0002 | 0.61 | 0.03 |
| | | Dorsal | <0.0001 | 0.03 | 0.0002 | 0.27 | 0.47 |
| | Medulla | Ventral | <0.0001 | 0.15 | <0.0001 | 0.94 | 0.13 |
| | | Dorsal | <0.0001 | 0.22 | <0.0001 | <0.0001 | 0.76 |
| Median (Range) Surface Area Rate of Change (mm²/year) | Brainstem | Total | <0.0001 | 0.11 | 0.002 | 0.92 | 0.30 |
| | | Ventral | <0.0001 | 0.13 | 0.002 | 0.997 | 0.20 |
| | | Dorsal | <0.0001 | 0.16 | 0.002 | 0.95 | 0.55 |
| | Midbrain | Total | <0.0001 | 0.81 | 0.001 | 0.94 | 0.32 |
| | | Ventral | 0.0006 | 0.91 | 0.02 | 0.997 | 0.89 |
| | | Dorsal | <0.0001 | 0.45 | 0.11 | 0.52 | 0.04 |
| | Pons | Total | <0.0001 | 0.02 | <0.0001 | 0.56 | 0.15 |
| | | Ventral | <0.0001 | 0.003 | <0.0001 | 0.47 | 0.03 |
| | | Dorsal | <0.0001 | 0.09 | <0.0001 | 0.90 | 0.66 |
| | Medulla | Total | <0.0001 | 0.13 | 0.0001 | 0.41 | 0.74 |
| | | Ventral | <0.0001 | 0.06 | 0.0004 | 0.47 | 0.58 |
| | | Dorsal | <0.0001 | 0.29 | <0.0001 | 0.45 | 0.89 |
| Median (Range) Pons Surface Complexity Rate of Change (mm/year) | | Ventral | <0.0001 | <0.0001 | 0.006 | 0.71 | 0.88 |
| | | Dorsal | <0.0001 | 0.02 | <0.0001 | 0.007 | 0.49 |

For each of the brainstem structures, African American non-progressive MS patients exhibited greater volume and surface area reductions than white non-progressive MS patients. FIGS. 7A-7C, 8A-8C, 9A-9C, 10A-10C, and 11A-11C—showing 3D representations of a healthy patient, an African American non-progressive MS patient, an African American progressive MS patient, a white non-progressive MS patient, and a white progressive MS patient, respectively—illustrate these trends, with volume preservation exhibited in the brainstems of the healthy and white non-progressive MS patients (FIGS. 7B-7C and 10B-10C) and atrophy exhibited in the brainstems of the African American non-progressive MS, African American progressive MS, and white progressive MS patients (FIGS. 8B-8C, 9B-9C, and 11B-11C). African American non-progressive MS patients also exhibited greater grey matter volume reductions and larger T2-weighted lesion volume increases than white non-progressive MS patients. These differences were statistically significant.

For mean curvature, in the ventral region of the pons there were statistically-significant differences between each of the cohorts, allowing for stratification thereof (FIG. 6). African American non-progressive MS patients also exhibited changes in ventral mean curvature that trended more so toward concavity than white non-progressive MS patients. In the dorsal region of the pons, African American non-progressive MS patients exhibited similar baseline mean curvatures as progressive MS patients, with the change in dorsal mean curvature being larger (e.g., a greater shift toward convexity) for white non-progressive MS patients than for African American non-progressive MS patients.

Example 2

A portion of a brainstem was analyzed for each of 35 patients using 3D MRI. The patients were placed into a healthy control group and two MS groups. The patients in the healthy control group had no history of brain anomalies typical for CNS demyelination based on the observed radiological phenotype and formal imaging interpretations by board certified neuroradiologists and clinical impressions by specialists in MS. The patients in each of the MS groups had a confirmed diagnosis of relapsing-remitting non-progressive MS (with an EDSS score that was less than 2.0) based on established criteria, results from supporting para-clinical studies (i.e., cerebrospinal fluid profiles, electrophysiological data, serological results), and the exclusion of other disease states. The patients of a first one of the MS groups were African Americans and the patients of a second one of the MS groups were white.

All imaging studies were performed on a 3T MRI scanner (Philips Medical Systems, Cleveland, OH) using a 32-channel phased array coil for reception and body coil for transmission. Each MRI study included scout localizers, 3D high-resolution inversion recovery spoiled gradient-echo T1-weighted isotropic ($1.1 \times 1.1 \times 1.1$ mm$^3$, TE/TR/TI=3.7/8.1/864 ms, flip angle 12 degrees, $256 \times 220 \times 170$ mm$^3$ FOV, number of excitations (NEX)=1, 170 slices, duration: 4:11 min), 3D fluid-attenuated inversion recovery (FLAIR) ($1.1 \times 1.1 \times 1.1$ mm$^3$, TE/TR/TI=350/4800/1600 ms, flip angle 90 degrees, $250 \times 250 \times 180$ mm$^3$ FOV, NEX=1, 163 slices, duration: 5:02 min) and 3D T2-weighted sequence acquired in sagittal plane ($1.0 \times 1.0 \times 1.0$ mm$^3$, TE/TR/TI=229/2500/1600 ms, flip angle 90 degrees, $250 \times 250 \times 180$ mm$^3$ FOV, NEX=1, 164 slices, duration: 4:33 min).

The MRI images were segmented and analyzed without knowledge of demographic data, clinical history, current or past treatments, or disease duration. MRI registration was initially performed based on structural positioning and intensity using an in-house software package (Med-IP) and were aligned using the Insight Toolkit (ITK) (version 5.1.1;

Kitware Clifton Park, N.Y., U.S.A.), and multi-resolution rigid registration was performed with Mattes Mutual Information Metric. To ensure proper intensity alignment, histogram matching of intensities involving regions of interest through linear transforms and ordered correspondence on a set of match points computed from the quantiles of each histogram were performed.

The region of interest was a portion of the brainstem that measured 25 mm from the medulla to the caudal region of the C2 (medulla-upper cervical spinal cord). It was isolated from the 3D T1-weighted MRI images using Materialise Mimics (version 22.0; Materialise NV, Leuven, Belgium). For each patient, the 3D representation of the medulla-upper cervical spinal cord was obtained at a first time and at a second time that was after the first time. Masks were generated from both MRI time points. Additionally, each 3D representation of the medulla-upper cervical spinal cord was segmented into ventral and dorsal portions based on centroid measures.

A number of geometric characteristics were calculated. For example, for each patient and at each time point, the volume and surface area of the medulla-upper cervical spinal cord and the ventral and dorsal portions thereof were determined. Temporal changes in volume and surface area were also determined. Volume changes were measured in the same manner that they were in EXAMPLE 1. Additionally, for each of the 3D representations, mean curvature (surface complexity) was determined for an 8 mm×6.25 mm×9 mm region of each of the ventral and dorsal portions of the medulla-upper cervical spinal cord. The mean curvature calculation was performed using Materialise Mimics using the same technique as in EXAMPLE 1.

Figure 12:
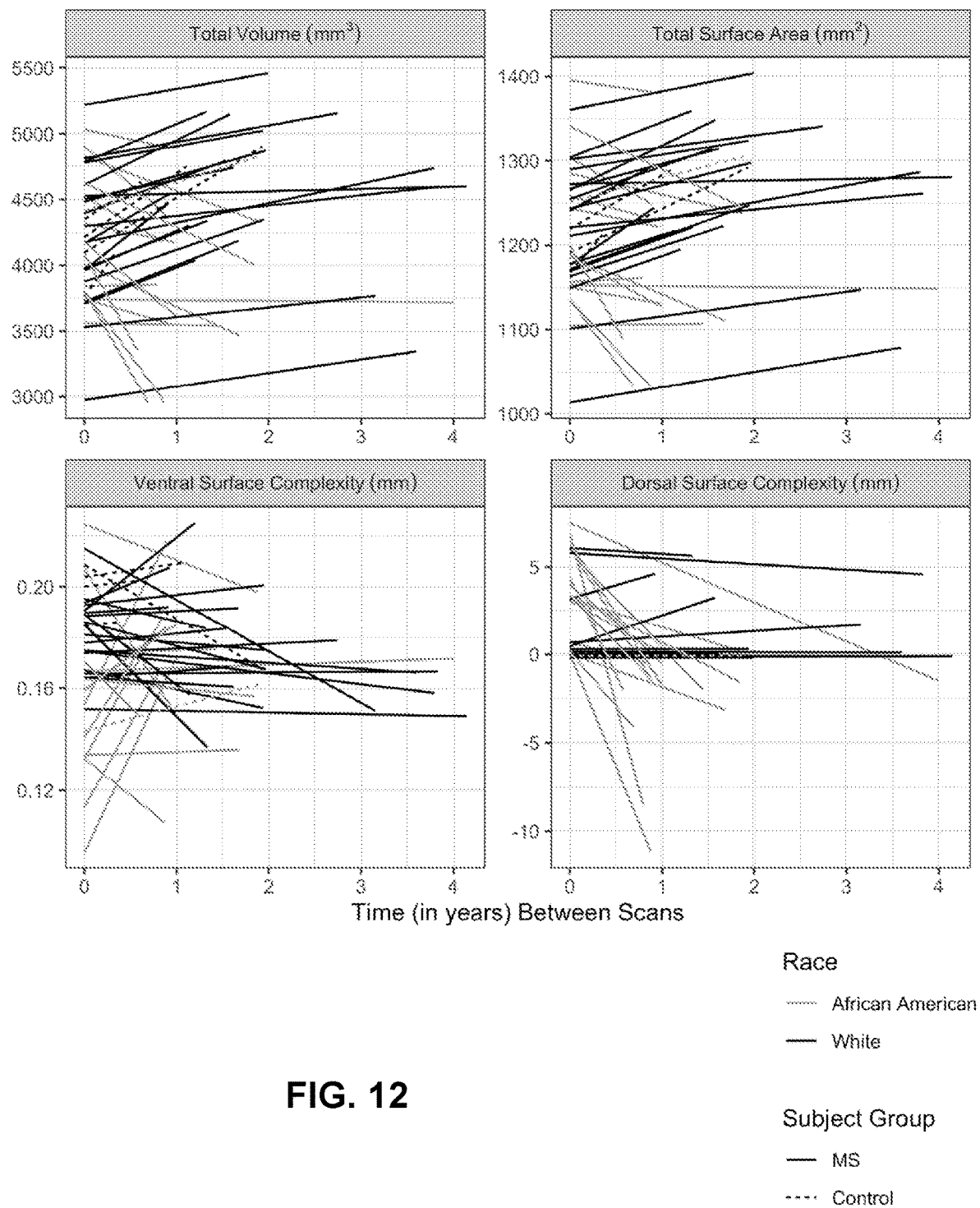
FIG. 12 is a set of graphs showing volume, surface area, mean curvature (surface complexity) of the ventral portion, and mean curvature (surface complexity) of the dorsal portion of the medulla and upper cervical spinal cord.
Figure 13:
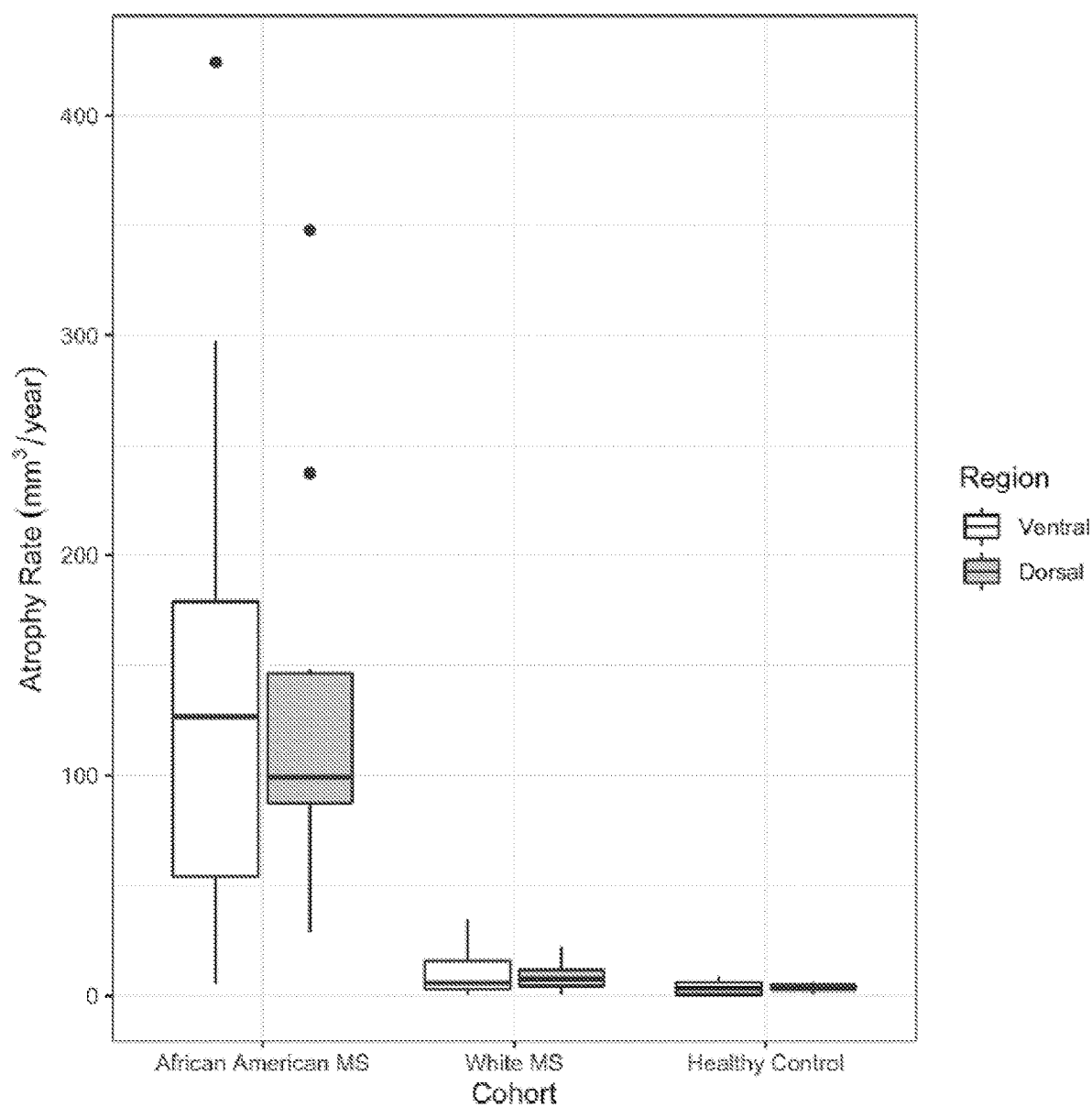
FIG. 13 is a box chart showing atrophy rates of the ventral and dorsal portions of the medulla and upper cervical spinal cord for African American non-progressive MS patients, white non-progressive MS patients, and healthy patients.

TABLES 5-7, below, set forth the clinical data and the geometric data of the medulla-upper cervical spinal cord for the healthy patients, African American non-progressive MS patients, and white non-progressive MS patients, respectively. TABLE 8, below, sets forth the p-values reflecting the level of significance of differences between certain cohorts. A p-value less than 0.05 was considered statistically significant. FIG. 12 also includes graphs showing geometric characteristics of the analyzed portions of the brainstem, and FIG. 13 is a box chart illustrating the atrophy rate of the different cohorts.

TABLE 5

Clinical and Medulla-Upper Cervical Spinal Cord Geometric Data for Healthy Patients

| | | |
|---|---|---|
| Subjects | | 5 |
| Median (IQR)* Age | | 51.8 (10.23) |
| Female | | 2 |
| Median (IQR) Time to Initial Treatment (years) | | — |
| Median (IQR) Time Between Scans | | 1.11 (1.27) |
| EDSS Score | | — |
| Median (IQR) Volume (mm$^3$) | First Time | 4214.5 (251.94) |
| | Second Time | 4750.75 (192.36) |
| Median (IQR) Rate of Change in Volume (mm$^3$/year) | | 461.19 (69.13) |
| Median (IQR) Surface Area (mm$^2$) | First Time | 1219.22 (49.73) |
| | Second Time | 1289.79 (18.24) |
| Median (IQR) Change in Surface Area (mm$^2$) | | 53.39 (11.7) |
| Median (IQR) Ventral Surface Area (mm$^2$) | | 620.05 (39.9) |
| Median (IQR) Ventral Volume (mm$^3$) | | 2164.89 (118.89) |
| Median (IQR) Dorsal Surface Area (mm$^2$) | | 605.08 (7.27) |
| Median (IQR) Dorsal Volume (mm$^3$) | | 2049.62 (62.5) |
| Median (IQR) Compliance Rate (mm$^3$/year) | Ventral | 202.89 (68.57) |
| | Dorsal | 207.15 (62.01) |
| | Total | 470.56 (70.06) |
| Median (IQR) Atrophy Rate (mm$^3$/year) | Ventral | 2.92 (5.63) |
| | Dorsal | 3.03 (2.11) |
| | Total | 5.69 (8.48) |
| Median (IQR) Dorsal Surface Complexity (mm) | First Time | −0.08 (0.16) |
| | Second Time | −0.05 (0.06) |
| Median (IQR) Rate of Change in Dorsal Surface Complexity (mm/year) | | −0.04 (0.03) |
| Median (IQR) Ventral Surface Complexity (mm) | First Time | 0.2 (0.02) |
| | Second Time | 0.19 (0.04) |
| Median (IQR) Rate of Change in Ventral Surface Complexity (mm/year) | | 0 (0) |

*Interquartile range

TABLE 6

Clinical and Medulla-Upper Cervical Cord Geometric Data for African American Non-Progressive MS Patients

| | | |
|---|---|---|
| Subjects | | 10 |
| Median (IQR) Age | | 33.8 (10.86) |
| Female | | 8 |
| Median (IQR) Time to Initial Treatment (years) | | 0.08 (1.3) |
| Median (IQR) Time Between Scans | | 0.99 (0.74) |
| EDSS Score (at First and Second Times) | | 0.0 (0.00-0.00) |
| Median (IQR) Volume (mm$^3$) | First Time | 4164.11 (976.51) |
| | Second Time | 4015.58 (711.4) |
| Median (IQR) Rate of Change in Volume (mm$^3$/year) | | −180.52 (261.26) |
| Median (IQR) Surface Area (mm$^2$) | First Time | 1215.66 (124.15) |
| | Second Time | 1191.36 (101.16) |
| Median (IQR) Change in Surface Area (mm$^2$) | | −21.04 (23.67) |
| Median (IQR) Ventral Surface Area (mm$^2$) | | 607.81 (68.82) |
| Median (IQR) Ventral Volume (mm$^3$) | | 2056.27 (418.21) |
| Median (IQR) Dorsal Surface Area (mm$^2$) | | 606.85 (59.21) |
| Median (IQR) Dorsal Volume (mm$^3$) | | 2107.84 (434.51) |
| Median (IQR) Compliance Rate (mm$^3$/year) | Ventral | 20.47 (28.54) |
| | Dorsal | 25.47 (12.57) |
| | Total | 52.34 (32.57) |
| Median (IQR) Atrophy Rate (mm$^3$/year) | Ventral | 126.81 (124.97) |
| | Dorsal | 99.09 (59.07) |
| | Total | 244.36 (203.04) |

TABLE 6-continued

Clinical and Medulla-Upper Cervical Cord Geometric Data
for African American Non-Progressive MS Patients

| | | |
|---|---|---|
| Median (IQR) | First Time | 3.58 (4.77) |
| Dorsal Surface Complexity (mm) | Second Time | −1.49 (2.39) |
| Median (IQR) Rate of Change in Dorsal Surface Complexity (mm/year) | | −3.74 (5.8) |
| Median (IQR) | First Time | 0.16 (0.04) |
| Ventral Surface Complexity (mm) | Second Time | 0.17 (0.02) |
| Median (IQR) Rate of Change in Ventral Surface Complexity (mm/year) | | 0.01 (0.06) |

TABLE 7

Clinical and Medulla-Upper Cervical Cord Geometric
Data for WhiteNon-Progressive MS Patients

| | | |
|---|---|---|
| Subjects | | 20 |
| Median (IQR) Age | | 35.6 (17.39) |
| Female | | 10 |
| Median (IQR) Time to Initial Treatment (years) | | 0 (1.76) |
| Median (IQR) Time Between Scans | | 1.8 (1.52) |
| EDSS Score (at First and Second Times) | | 0.0 (0.0-0.0) |
| Median (IQR) | First Time | 4236.78 (605.7) |
| Volume (mm$^3$) | Second Time | 4597.46 (579.63) |
| Median (IQR) Rate of Change in Volume (mm$^3$/year) | | 219.08 (155.98) |
| Median (IQR) | First Time | 1230.99 (97.17) |
| Surface Area (mm$^2$) | Second Time | 1283.48 (94.47) |
| Median (IQR) Change in Surface Area (mm$^2$) | | 31.85 (20.85) |
| Median (IQR) Ventral Surface Area (mm$^2$) | | 615.19 (55.94) |
| Median (IQR) Ventral Volume (mm$^3$) | | 2187.13 (391.85) |
| Median (IQR) Dorsal Surface Area (mm$^2$) | | 609.68 (42.18) |
| Median (IQR) Dorsal Volume (mm$^3$) | | 2061.67 (289.76) |
| Median (IQR) | Ventral | 88.3 (109.77) |
| Compliance Rate (mm$^3$/year) | Dorsal | 97.46 (104.11) |
| | Total | 231.13 (155.78) |
| Median (IQR) | Ventral | 5.63 (12.98) |
| Atrophy Rate (mm$^3$/year) | Dorsal | 7.57 (7.36) |
| | Total | 16.14 (12.65) |
| Median (IQR) | First Time | −0.06 (0.43) |
| Dorsal Surface Complexity (mm) | Second Time | −0.07 (0.77) |
| Median (IQR) Rate of Change in Dorsal Surface Complexity (mm/year) | | 0 (0.02) |
| Median (IQR) | First Time | 0.18 (0.02) |
| Ventral Surface Complexity (mm) | Second Time | 0.17 (0.03) |
| Median (IQR) Rate of Change in Ventral Surface Complexity (mm/year) | | 0 (0.01) |

TABLE 8

P-Values Between Groups

| | | AA MS vs. White MS | White MS vs. Healthy |
|---|---|---|---|
| Median (IQR) | First Time | 0.376 | 0.554 |
| Volume (mm$^3$) | Second Time | 0.058 | 0.543 |
| Median (IQR) Rate of Change in Volume (mm$^3$/year) | | <0.0001 | 0.088 |
| Median (IQR) | First Time | 0.323 | 0.742 |
| Surface Area (mm$^2$) | Second Time | 0.176 | 0.602 |
| Median (IQR) Change in Surface Area (mm$^2$) | | <0.0001 | 0.233 |
| Median (IQR) Ventral Surface Area (mm$^2$) | | 0.231 | 0.995 |
| Median (IQR) Ventral Volume (mm$^3$) | | 0.740 | 0.460 |
| Median (IQR) Dorsal Surface Area (mm$^2$) | | 0.432 | 0.570 |
| Median (IQR) Dorsal Volume (mm$^3$) | | 0.163 | 0.674 |
| Median (IQR) | Ventral | 0.002 | 0.235 |
| Compliance Rate (mm$^3$/year) | Dorsal | 0.0005 | 0.028 |
| | Total | 0.0008 | 0.086 |
| Median (IQR) | Ventral | <0.0001 | 0.576 |
| Atrophy Rate (mm$^3$/year) | Dorsal | <0.0001 | 0.028 |
| | Total | <0.0001 | 0.109 |
| Median (IQR) | First Time | 0.030 | 0.128 |
| Dorsal Surface Complexity (mm) | Second Time | 0.047 | 0.279 |
| Median (IQR) Rate of Change in Dorsal Surface Complexity (mm/year) | | <0.0001 | 0.401 |
| Median (IQR) | First Time | 0.082 | 0.682 |
| Ventral Surface Complexity (mm) | Second Time | 0.197 | 0.793 |
| Median (IQR) Rate of Change in Ventral Surface Complexity (mm/year) | | 0.081 | 0.165 |

Figure 14A:
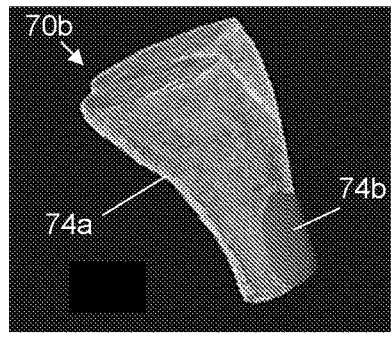
FIGS. 14A-14C each show 3D representations of a medulla and upper cervical spinal cord of an African American non-progressive MS patient at a first time (mesh) and at a second time (solid) superimposed on one another.
Figure 14B:
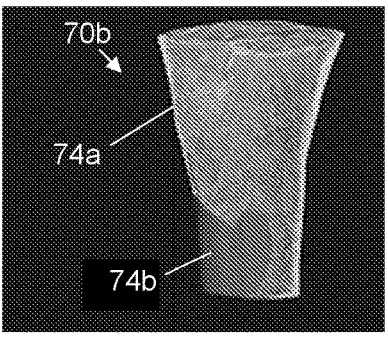
Figure 14C:
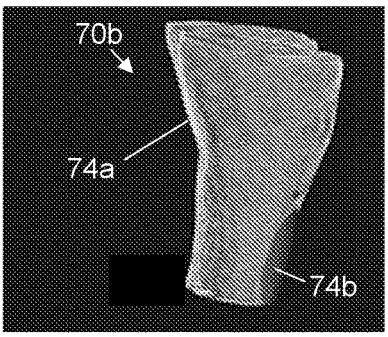
Figure 15A:
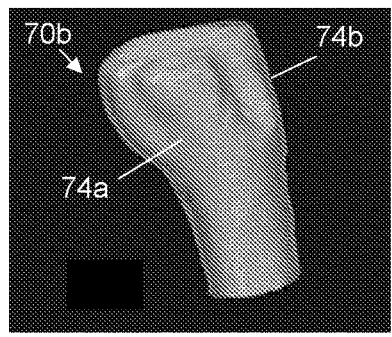
FIGS. 15A-15C each show 3D representations of a medulla and upper cervical spinal cord of a white non-progressive MS patient at a first time (solid) and at a second time (mesh) superimposed on one another.
Figure 15B:
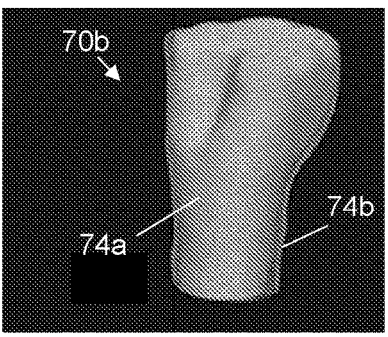
Figure 15C:
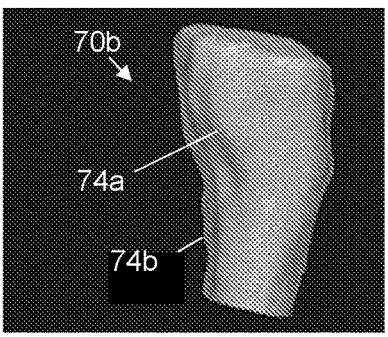
Figure 16A:
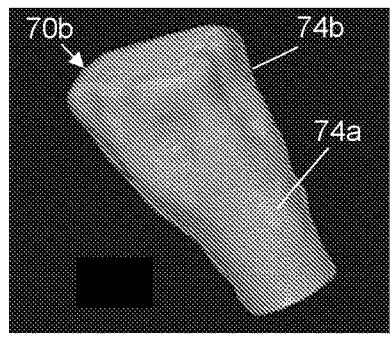
FIGS. 16A-16C each show 3D representations of a medulla and upper cervical spinal cord of a healthy patient at a first time (solid) and at a second time (mesh) superimposed on one another.
Figure 16B:
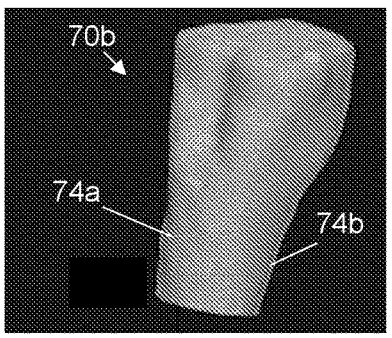
Figure 16C:
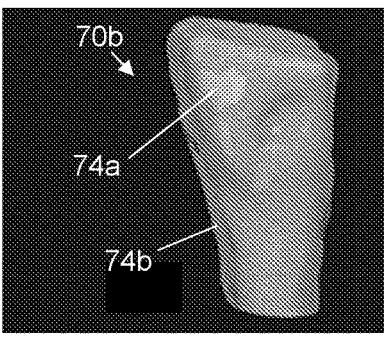

While there was no significant differences in baseline medulla-upper cervical spinal cord volume, African American MS patients experienced greater surface area reductions and greater rates of atrophy in the medulla-upper cervical spinal cord and its ventral and dorsal portions, compared to white MS patients. This is reflected in FIGS. 14A-14C, 15A-15C, and 16A-16C, which show 3D representations of the medulla-upper cervical spinal cord for three African American MS patients, three white MS patients, and three healthy patients, respectively. As shown, there was heterogeneous decreases in volume in the African American MS patients (FIGS. 14A-14C) while the other cohorts exhibited volume preservation (FIGS. 15A-15C and 16A-16C). African American MS patients were also more likely to have lower ventral and dorsal compliance rates (3D structural changes at the second time that were similar to or greater than the original baseline measures) compared to white MS patients.

Figure 17A:
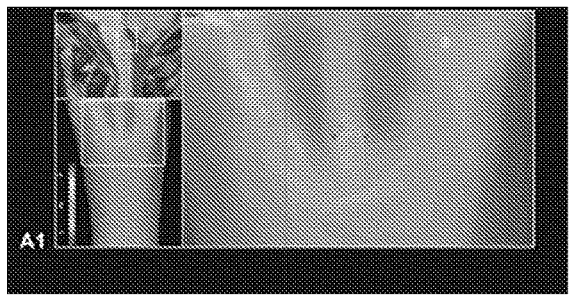
FIGS. 17A and 17B show curvature of a region of the dorsal portion of the medulla and upper cervical spinal cord of an African American non-progressive MS patient at first and second times, respectively.
Figure 17B:
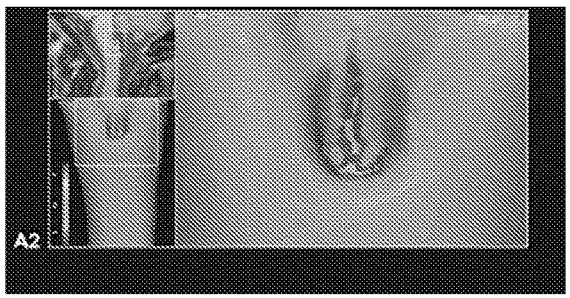
Figure 18A:
FIGS. 18A and 18B show curvature of a region of the dorsal portion of the medulla and upper cervical spinal cord of a white non-progressive MS patient at first and second times, respectively.
Figure 18B:
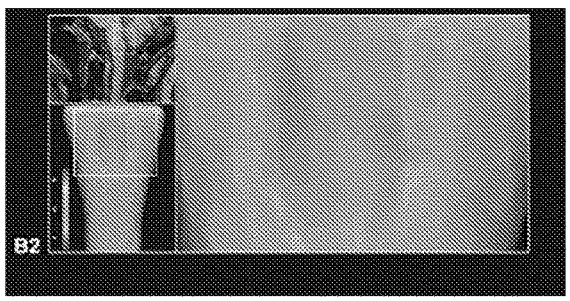
Figure 19A:
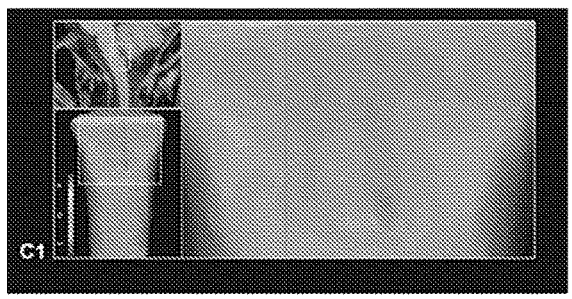
FIGS. 19A and 19B show curvature of a region of the dorsal portion of the medulla and upper cervical spinal cord of a healthy patient at first and second times, respectively.
Figure 19B:
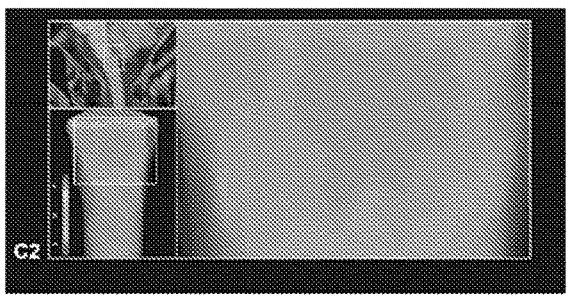

No significant differences in mean curvature (surface complexity) were identified in the ventral region of the medulla-upper cervical spinal cord that was analyzed between African American and white MS patients. However, in the dorsal region analyzed, there were statistically significant differences between these cohorts, with African Americans exhibiting changes in mean curvature reflecting an evolution to a more concave surface over time, compared to white MS patients. All African American MS patients exhibited this decrease in dorsal mean curvature. This is reflected in FIGS. 17A-17B, 18A-18B, and 19A-19B, which show curvature in the dorsal region of the medulla-upper cervical spinal cord of an African American MS patient, a white MS patient, and a healthy patient, respectively, at the first time (FIGS. 17A, 18A, and 19A) and the second time (FIGS. 17B, 18B, 19B). The African American MS patient exhibited a transition to a more concave surface (FIGS. 17A and 17B) compared to the other cohorts in which there were minimal changes in mean curvature (FIGS. 18A, 18B, 19A, and 19B).

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A method of analyzing one or more sections of a central nervous system of a patient, the method comprising:
   for each of the section(s), from data that includes one or more 3-dimensional (3D) representations of the section:
      segmenting each of the 3D representation(s) into ventral and dorsal portions; and
      for at least one of the 3D representation(s), determining a mean curvature of at least a region of a surface of the dorsal portion and/or a mean curvature of at least a region of a surface of the ventral portion;
   wherein each of the section(s) includes at least a portion of a brainstem of the patient.

2. The method of claim 1, wherein a first one of the section(s) includes a pons of the patient.

3. The method of claim 2, comprising characterizing whether the patient has multiple sclerosis and/or a type of multiple sclerosis in the patient based at least in part on the mean curvature of the region of the surface of the dorsal portion of the first section and/or the mean curvature of the region of the surface of the ventral portion of the first section.

4. The method of claim 3, wherein:
   the characterizing comprises determining that the patient has progressive multiple sclerosis; and
   for the first section:
      the mean curvature of the region of the surface of the dorsal portion is greater than or equal to −1.0 millimeters (mm); and/or
      the mean curvature of the region of the surface of the ventral portion is less than or equal to −2.0 mm.

5. The method of claim 3, wherein:
   the characterizing comprises determining that the patient has relapsing-remitting multiple sclerosis;
   for the first section, the mean curvature of the region of the surface of the dorsal portion is less than −1.0 millimeters (mm); and
   the patient is white.

6. The method of claim 2, comprising determining whether the mean curvature of the region of the surface of the ventral portion of the first section is:
   between 0.10 and 0.40 mm;
   between 0 and 0.60 mm;
   between −1.25 and −0.10 mm;
   between −4.50 and −2.0 mm; and/or
   between −8.0 and −5.0 mm.

7. The method of claim 2, wherein:
   for each of the section(s), the one or more 3D representations include a 3D representation of the section at a first time and a 3D representation of the section at a second time that is after the first time;
   the method comprises determining:
      a rate of change, from the first time to the second time, in the mean curvature of the region of the surface of the dorsal portion of the first section; and/or
      a rate of change, from the first time to the second time, in the mean curvature of the region of the surface of the ventral portion of the first section.

8. The method of claim 7, comprising characterizing whether the patient has multiple sclerosis and/or a type of multiple sclerosis in the patient based at least in part on:
   the rate of change in the mean curvature of the region of the surface of the dorsal portion of the first section; and/or
   the rate of change in the mean curvature of the region of the surface of the ventral portion of the first section.

9. The method of claim 7, comprising characterizing an efficacy of a treatment administered to the patient based at least in part on:
the rate of change in the mean curvature of the region of the surface of the dorsal portion of the first section; and/or
the rate of change in the mean curvature of the region of the surface of the ventral portion of the first section.

10. The method of claim 7, comprising, for the first section, for at least one of the rate of change in the mean curvature of the region of the surface of the dorsal portion and the rate of change in the mean curvature of the region of the surface of the ventral portion, comparing the rate of change to a baseline rate of change.

11. The method of claim 3, wherein the characterizing is further based at least in part on an ethnicity of the patient.

12. The method of claim 1, wherein one of the section(s) includes a medulla and an upper cervical spinal cord of the patient.

13. The method of claim 12, comprising characterizing whether the patient has multiple sclerosis and/or a type of multiple sclerosis in the patient based at least in part on the mean curvature of the surface of the dorsal portion of the section that includes the medulla and the upper cervical spinal cord.

14. The method of claim 13, wherein:
the characterizing comprises determining that the patient has multiple sclerosis;
for the section that includes the medulla and the upper cervical spinal cord, the mean curvature of the region of the surface of the dorsal portion is greater than or equal to 1.0 millimeter (mm); and
the patient is Black.

15. The method of claim 12, wherein:
for each of the section(s), the one or more 3D representations include a 3D representation of the section at a first time and a 3D representation of the section at a second time that is after the first time; and
the method comprises determining a rate of change, from the first time to the second time, in the mean curvature of the region of the surface of the dorsal portion of the section that includes the medulla and the upper cervical spinal cord.

16. The method of claim 15, comprising characterizing whether the patient has multiple sclerosis and/or a type of multiple sclerosis in the patient based at least in part on the rate of change in the mean curvature of the region of the surface of the dorsal portion of the section that includes the medulla and the upper cervical spinal cord.

17. The method of claim 16, wherein:
the characterizing comprises determining that the patient has non-progressive multiple sclerosis;
the rate of change in the mean curvature of the region of the surface of the dorsal portion of the section that includes the medulla and the upper cervical spinal cord is less than or equal to −1.0 millimeter (mm) per year; and
the patient is black.

18. The method of claim 15, comprising comparing the rate of change in the mean curvature of the region of the surface of the dorsal portion of the section that includes the medulla and the upper cervical spinal cord to a baseline rate of change.

19. The method of claim 1, wherein for each of the section(s), the dorsal and ventral portions each have a volume that is between 40% and 60% of a volume of the section.

20. The method of claim 1, comprising, from the data, determining:
a rate of change, from a first time to a second time that is after the first time, in a volume of at least a portion of the brainstem of the patient; and/or
a rate of change, from the first time to the second time, in a surface area of at least a portion of the brainstem of the patient.

21. The method of claim 20, comprising:
determining that the patient has non-progressive multiple sclerosis;
wherein the patient is Black; and
wherein:
the rate of change in the volume is less than or equal to 0 cubic millimeters ($mm^3$) per year; and/or
the rate of change in the surface area is less than or equal to 0 square millimeters ($mm^2$) per year.

22. The method of claim 1, wherein the data comprises one or more magnetic resonance imaging (MRI) images that comprise the 3D representation(s) of the section(s).

23. The method of claim 1, wherein for each of the section(s):
each of the 3D representation(s) of the section comprises a polyhedron having a plurality of polygonal faces; and
for at least one of the dorsal and ventral portions of at least one of the 3D representation(s) of the section, determining the mean curvature of the region of the portion comprises:
calculating a curvature of each of the polygonal faces of the region of the portion of the 3D representation based at least in part on a curvature calculated at each of a plurality of vertices of the polygonal face; and
averaging the maximum curvatures of the polygonal faces of the region of the portion of the 3D representation.

24. A system for analyzing one or more sections of a central nervous system of a patient, the system comprising one or more processors configured to:
for each of the section(s), from data that includes one or more 3-dimensional (3D) representations of the section:
segment each of the 3D representation(s) into ventral and dorsal portions; and
for at least one of the 3D representation(s), determine a mean curvature of at least a region of a surface of the dorsal portion and/or a mean curvature of at least a region of a surface of the ventral portion;
wherein each of the section(s) includes at least a portion of a brainstem of the patient.

25. The system of claim 24, wherein:
a first one of the section(s) includes a pons of the patient; and
the processor(s) are configured to characterize whether the patient has multiple sclerosis and/or a type of multiple sclerosis in the patient based at least in part on an ethnicity of the patient and:
the mean curvature of the region of the surface of the dorsal portion of the first section; and/or
the mean curvature of the region of the surface of the ventral portion of the first section.

26. The system of claim 25, wherein the processor(s) are configured to determine that the patient has progressive multiple sclerosis when:
the mean curvature of the region of the surface of the dorsal portion of the first section is greater than or equal to −1.0 millimeters (mm); and/or the mean curvature of the region of the surface of the ventral portion of the first section is less than or equal to −2.0 mm.

27. The system of claim 24, wherein:
a first one of the section(s) includes a pons of the patient; and
the processor(s) are configured to determine whether the mean curvature of the region of the surface of the ventral portion of the first section is:
between 0.10 and 0.40 mm;
between 0 and 0.60 mm;
between −1.25 and −0.10 mm;
between −4.50 and −2.0 mm; and/or
between −8.0 and −5.0 mm.

28. The system of claim 24, wherein:
for each of the section(s), the one or more 3D representations include a 3D representation of the section at a first time and a 3D representation of the section at a second time that is after the first time;
the processor(s) are configured to determine, for each of the section(s):
a rate of change, from the first time to the second time, in the mean curvature of the region of the surface of the dorsal portion of the section; and/or
a rate of change, from the first time to the second time, in the mean curvature of the region of the surface of the ventral portion of the section.

29. The system of claim 28, wherein:
a first one of the section(s) includes a pons of the patient; and
the processor(s) are configured to characterize whether the patient has multiple sclerosis and/or the type of multiple sclerosis in the patient based at least in part on the rate of change in the mean curvature of the region of the surface of the dorsal portion of the first section and/or the rate of change in the mean curvature of the region of the surface of the ventral portion of the first section.

30. The system of claim 28, wherein:
a first one of the section(s) includes a pons of the patient; and;
the processor(s) are configured to, for the first section, for at least one of the rate of change in the mean curvature of the region of the surface of the dorsal portion and the rate of change in the mean curvature of the region of the surface of the ventral portion, compare the rate of change to a baseline rate of change.

31. The system of claim 24, wherein:
one of the section(s) includes a medulla and an upper cervical spinal cord of the patient; and
the processor(s) are configured to characterize whether the patient has multiple sclerosis and/or a type of multiple sclerosis in the patient based at least in part on the mean curvature of the region of the surface of the dorsal portion of the section that includes the medulla and the upper cervical spinal cord.

32. The system of claim 31, wherein:
for each of the section(s), the one or more 3D representations include a 3D representation of the section at a first time and a 3D representation of the section at a second time that is after the first time; and
the processor(s) are configured to determine a rate of change, from the first time to the second time, in the mean curvature of the region of the surface of the dorsal portion of the section that includes the medulla and the upper cervical spinal cord; and
the processor(s) are configured to:
characterize whether the patient has multiple sclerosis and/or the type of multiple sclerosis in the patient based at least in part on the rate of change in the mean curvature of the region of the surface of the dorsal portion of the section that includes the medulla and the upper cervical spinal cord; and/or
compare the rate of change in the mean curvature of the region of the surface of the dorsal portion of the section that includes the medulla and the upper cervical spinal cord to a baseline rate of change.

* * * * *